United States Patent [19]
Choi et al.

[11] Patent Number: 5,892,088
[45] Date of Patent: *Apr. 6, 1999

[54] SULFAMATE COMPOUND CONTAINING N-SUBSTITUTED CARBAMOYL GROUP AND METHOD FOR PREPARING THE SAME

[75] Inventors: Yong Moon Choi, Towaco, N.J.; Dong Il Han; Hyung Cheol Kim, both of Taejon, Rep. of Korea

[73] Assignee: Yukong Limited, Seoul, Rep. of Korea

[ * ] Notice: The term of this patent shall not extend beyond the expiration date of Pat. No. 5,654,461.

[21] Appl. No.: 742,929

[22] Filed: Nov. 1, 1996

Related U.S. Application Data

[63] Continuation-in-part of Ser. No. 616,077, Mar. 14, 1996, Pat. No. 5,654,461.

[30] Foreign Application Priority Data

Nov. 2, 1995 [KR] Rep. of Korea ............... 95-39456
Oct. 28, 1996 [KR] Rep. of Korea ............... 96-49052

[51] Int. Cl.$^6$ ............... C07C 309/14; C07C 309/63; C07C 311/05
[52] U.S. Cl. ............... 558/48; 558/52; 558/53
[58] Field of Search ............... 558/48, 52, 53

[56] References Cited

U.S. PATENT DOCUMENTS

| | | | |
|---|---|---|---|
| 4,792,569 | 12/1988 | Maryanoff et al. | 514/517 |
| 5,384,327 | 1/1995 | Costanzo et al. | 514/456 |
| 5,510,379 | 4/1996 | Lee et al. | 514/517 |
| 5,654,461 | 8/1997 | Choi et al. | 558/48 |

FOREIGN PATENT DOCUMENTS

WO94/14827  7/1994  WIPO ............... A61K 31/70

OTHER PUBLICATIONS

Maryanoff et al., J. Med. Chemistry, 30, 880–887 (1987).

*Primary Examiner*—Johann Richter
*Assistant Examiner*—Taofiq A. Solola
*Attorney, Agent, or Firm*—Gibbons, Del Deo, Dolan, Griffinger & Vecchione

[57] ABSTRACT

There are disclosed novel sulfamate compounds containing N-substituted carbomoyl group including their racemates and (R)- and (S)-optical isomers represented by Formulas I, II and III, pharmaceutically useful for the prophylaxis and treatment of the disorders of the central nervous system, especially for nervous myalgia, epilepsy and minimal brain dysfunction:

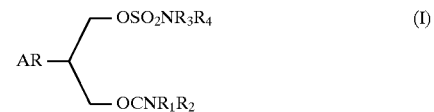

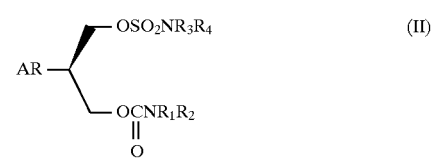

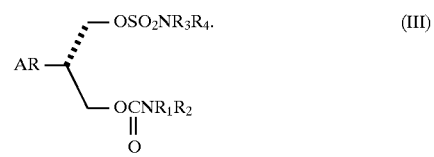

3 Claims, No Drawings

SULFAMATE COMPOUND CONTAINING N-SUBSTITUTED CARBAMOYL GROUP AND METHOD FOR PREPARING THE SAME

This is a CIP of application Ser. No. 08/616,077 filed Mar. 14, 1996 now U.S. Pat. No. 5,654,461.

BACKGROUND OF THE INVENTION

1. Field of the Invention

The present invention relates to pharmaceutically useful sulfamate compounds containing N-substituted carbamoyl group and, more particularly, to N,N'-substituted carbamoyl-2-aryl propanol sulfamates including their racemates and (R)- and (S)-optical isomers, useful for the prophylaxis and treatment of the disorders of the central nervous system. Also, the present invention is concerned with methods for preparing the same.

2. Description of the Prior Art

Sulfamate compounds are well known to be useful as medicines for controlling various central nervous system (CNS) disorders, especially as antiepileptic.

As a prior art relating to these compounds, fructopyranose sulfamate compounds are reported in J. Med. Chem. 30, 880–887(1987), together with their pharmaceutical effects. Other pharmaceutically useful sulfamates are also known. For example, sorbopyranose sulfamates and penethylsulfamates are disclosed in PCT WO 14827 and U.S. Pat. No. 4.792,569, respectively, These compounds have effectively been used as therapeutical medicines for managing CNS diseases, such as an antiepileptic. Active research and development efforts have been and continue to be directed to the application of sulfamate compounds for CNS disorders.

SUMMARY OF THE INVENTION

As a result of intensive and thorough research for the sulfamate derivatives of 2-aryl-1,3-propanediol, the present inventors found that the compounds introduced with N-substituted carbamoyl group are pharmaceutically useful in prophylaxis and treatment of CNS disorders.

Accordingly, it is an objective of the present invention to provide novel N-substituted carbamoyl-containing sulfamate compounds effective for the prophylaxis and treatment of CNS disorders. These sulfamate compounds comprise racemates represented by the following Formula I and their (R)- and (S)-optical isomers represented by the following Formulas II and III, respectively:

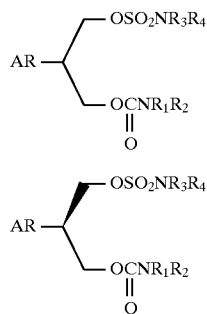

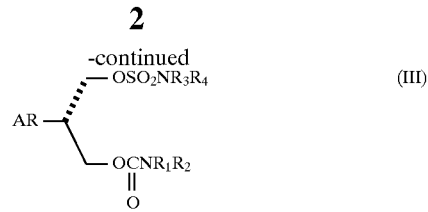

wherein, Ar is represented by the following formulas:

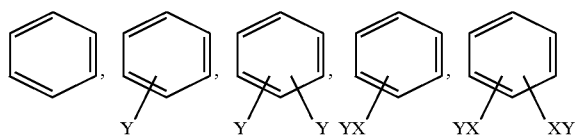

Y is selected from the group consisting of halogens such as F, Cl, Br and I, trifluoromethyl and alkyl groups containing 1 to 3 carbon atoms when Y alone binds to benzene ring and from the group consisting of trifluoromethyl and alkyl groups containing 1 to 3 carbon atoms when Y binds to X which is O or S; and $R_1$, $R_2$, $R_3$ and $R_4$, identical or different, each are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_1R_2$ and $NR_3R_4$, identical or different, each may form a 3 to 7-membered aliphatic cyclic compound together with another nitrogen atom or oxygen atom.

Because the N,N'-substituted carbamoyl 2-aryl propanol sulfamate represented by Formula I has, a chiral center at the benzyl position, they may be in either (R)- or (S)-optical isomer. In vivo, an optical isomer of one compound may exhibit even better pharmaceutical effect than other optical isomers, and many examples of the optical effect have been reported. Recent trend is to use optical isomers to develop new medicines. Thus, it is very important to separate the racemic mixture of one compound into respective optical isomers and apply them for pharmacology. Based upon this fact, the present inventors found that their (R)- and (S)-optical isomers are very effective for the prophylaxis and treatment of the disorders of the central nervous system, especially as antiepileptic, acute ischemic stroke and neuroprotective.

It is another objective of the present invention to provide methods for preparing the N,N'-substituted carbamoyl-2-aryl propanol sulfamate racemates and their pure (R)- and (S)-optical isomers.

It is a further objective of the present invention to provide the intermediates useful for producing the N,N-substituted carbamoyl-2-aryl propanol sulfamate racemates represented by Formula I, including 3-N-substituted carbamoyl-2-aryl propanol acetate represented by the following formula IV:

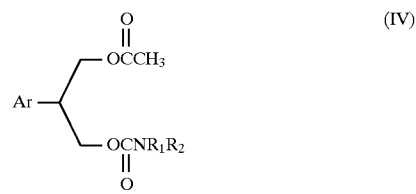

wherein Ar, $R_1$ and $R_2$ are as defined above, 3-N-substituted carbamoyl-2-aryl propanol represented by the following formula V:

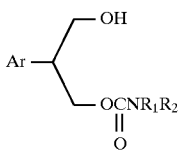

(V)

wherein Ar, $R_1$ and $R_2$ are as defined above, 3-acetoxy-2-aryl propanol sulfamate represented by the following formula VI;

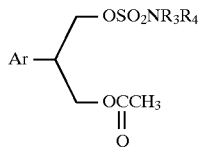

(VI)

wherein Ar, $R_3$ and $R_4$ are as defined above, 2-aryl-1,3-propandiol monosulfamate represented by the following formula VII:

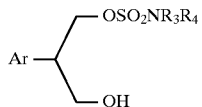

(VII)

wherein Ar, $R_3$, and $R_4$ are as defined above; the intermediates useful for producing the (R)-N,N'-substituted carbamoyl-2-aryl propanol sulfamate represented by Formula II including (S)-3-N-substituted carbamoyl-2-aryl propanol acetate represented the following formula VIII:

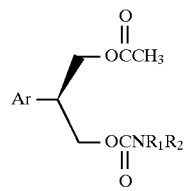

(VIII)

wherein Ar, $R_1$ and $R_2$ are as defined above with the proviso that $R_1$ and $R_2$ are not hydrogen atoms simultaneously, and (S)-3-N-substituted carbamoyl-2-aryl propanol represented by the following formula IX:

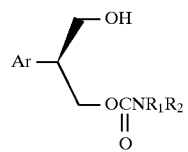

(IX)

wherein Ar, $R_1$ and $R_2$ are as defined above with the proviso that $R_1$ and $R_2$ are not hydrogen atoms simultaneously; and the intermediates useful for producing the (S)-N,N'-substituted carbamoyl-2-aryl-propanol sulfamate represented by Formula III including the (S)-3-acetoxy-2-aryl-1, 3-propandiol sulfamate represented by the following formula X:

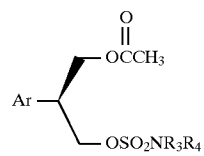

(X)

wherein Ar, $R_3$ and $R_4$ are as defined above, the (S)-2-aryl-1,3-propandiol monosulfamate represented by the following formula XI:

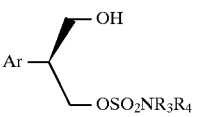

(XI)

wherein Ar, $R_3$, and $R_4$ are as defined above, (R)-3-N-substituted carbamoyl-2-aryl propanol acetate represented by the following formula XII:

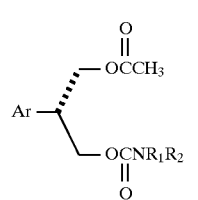

(XII)

wherein Ar, $R_1$ and $R_2$ are as defined above with the proviso that $R_1$ and $R_2$ are not hydrogen atoms simultaneously, and (R)-3-N-substituted carbamoyl-2-aryl propanol represented by the following structural formula XIII:

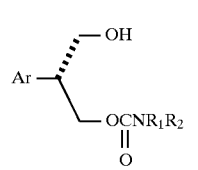

(XIII)

wherein Ar, $R_1$ and $R_2$ are as defined above with the proviso that $R_1$ and $R_2$ are not hydrogen atoms simultaneously For accomplishing the above objectives, there are provided the N,N'-substituted carbamoyl-2-aryl propanol sulfamate racemates represented by the following formula I:

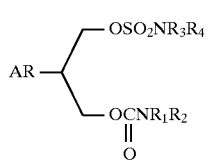

(I)

wherein Ar is represented by the following formulas;

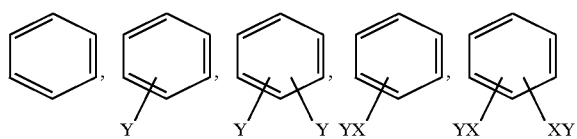

Y is selected from the group consisting of halogens such as F, Cl, Br and I, trifluoromethyl and alkyl groups containing 1 to 3 carbon atoms when Y alone binds to benzene ring and from the group consisting of trifluoromethyl and alkyl groups containing 1 to 3 carbon atoms when Y binds to X which is O or S;

$R_1$, $R_2$, $R_3$ and $R_4$, identical or different, each are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_1R_2$ and $NR_3R_4$, identical or different, each may form a 3 to 7-membered aliphatic cyclic compound together with another nitrogen atom or oxygen atom.

The N,N-substituted carbamoyl-2-aryl propanol sulfamate compounds represented by Formula I can be prepared by the following three methods, in accordance with the present invention.

A detailed description will be given of a first method below, in conjunction with reaction schemes.

First, the 3-acetoxy-2-aryl propanol of Formula XIV is reacted with carbonyl diimidazole in dichloromethane solution to give the 3-imidazolyl carbonyloxy-2-aryl propanol acetate of Formula XV, which is, without purification, reacted with the substituted amine of Formula XVI to produce the 3-N-substituted carbamoyl-2-aryl propanol acetate of Formula IV, as shown in Reaction Scheme I:

Reaction Scheme I

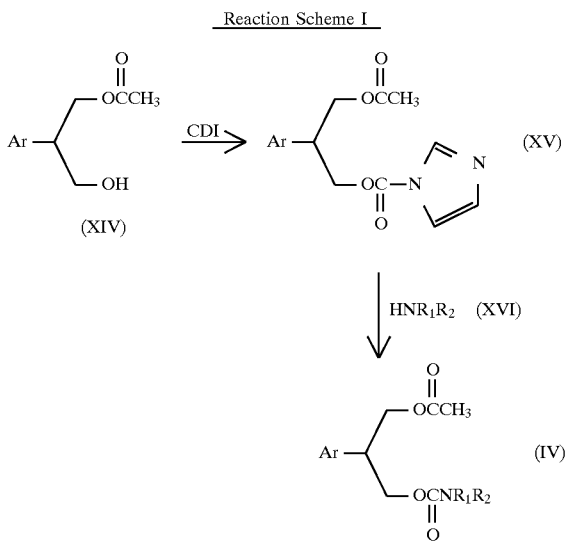

wherein Ar, $R_1$ and $R_2$ each are as defined above.

Detailed conditions for the above reactions are as follows,

The compound of Formula XIV, the starting material, is reacted preferably at an amount of about 0.1 to 2.0 moles with 1.1 to 2.5 equivalents of carbonyl diimidazole when considering yield and economical aspects. It is preferable that the former reaction of Reaction Scheme I is carried out at a temperature of −5° to 40° C. For example, if the reaction is performed at a temperature less than −5° C., the progress of the reaction is very slow. On the other hand, if it is carried out at a temperature higher than 40° C. the yield decreases due to side reactions. Useful solvents in this reaction include low hydrocarbon halide solvents, such as methylene chloride and chloroform, ethereal solvents, such as ethyl ether and tetrahydrofuran, and acetonitrile with preference to methylene chloride, chloroform and tetrahydrofuran.

In the preparation reaction of the compound of Formula IV from the compound of Formula XV, the substituted amine is used at an amount of 1.0 to 5.0 equivalents, in consideration of rapid reaction and after-treatment. This reaction is executed at a temperature ranging from 0° to 30° C. in a solvent selected from tetrahydrofuran and methylene chloride.

Next, the 3-N-substituted carbamoyl-2-aryl propanol acetate of Formula IV is subjected to transesterification in an alcohol solvent in the presence of a base catalyst, to give the 3-N-substituted carbamoyl-2-aryl propanol of the following formula V, as shown in Reaction Scheme II:

Reaction Scheme II

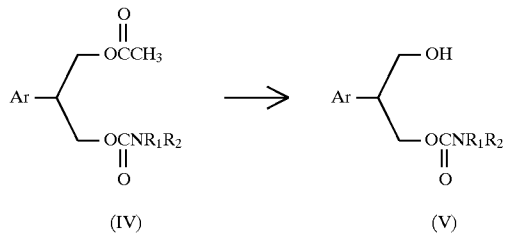

wherein Ar, $R_1$ and $R_2$ each are as defined above.

In the transesterification, the 3-N-substituted carbamoyl-2-aryl propanol acetate of Formula IV is used at an amount of 0.1 to 2.0 moles. As the base catalyst, sodium hydroxide, potassium hydroxide, sodium carbonate, lithium hydroxide, potassium carbonate, sodium bicarbonate or potassium cyanide is used at an amount of 0.1 to 1.0 equivalent at a temperature of 0° to 30° C. Useful solvents include methylalcohol, ethylalcohol and propylalcohol. Preferred is methylalcohol when considering the reaction yield and the removal convenience after completion of the reaction. Attention must be paid to the point that the base catalyst remained in the reaction mixture is required to be inactivated after the reaction. If the active base catalyst is remained, a reverse reaction occurs during after-treatment, returning the product into the starting material. For the inactivation of the base catalyst, a proper acidic material is added to the reaction mixture after the reaction has been completed. Preferred is 1N hydrochloric acid solution or saturated ammonium chloride solution.

In subsequence, the compound of Formula V is reacted with sulfamoyl chloride in the presence of a base catalyst, to prepare the N,N'-substituted carbamoyl-2-aryl propanol sulfamate. This reaction is depicted in Reaction Scheme III:

Reaction Scheme III

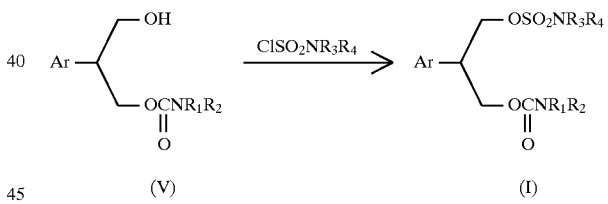

wherein Ar, $R_1$, $R_2$, and $R_3$ and $R_4$ are as defined above.

The 3-N-substituted carbamoyl-2-aryl propanol represented by Formula V is used at an amount of 0.1 to 2.0 moles. As the base catalyst, triethylamine, pyridine, antipyrin, or diisopropylethylamine is employed. Available reaction solvents include amide solvents, such as dimethylformamide, ethereal solvents, such as ethyl ether and tetrahydrofuran, and acetonitrile with preference to tetrahydrofuran and acetonitrile. It is preferable that this reaction is carried out at a temperature of −10° to 40° C. For example, if the reaction temperature is maintained below −10° C., the progress of the reaction is very slow. On the other hand, if the reaction is carried out at a temperature higher than 40° C., the yield lowers by the production of unknown by-products. When considering reaction progress, convenience in after-treatment and economical aspects, it is preferable that the base catalyst and the sulfamoyl chloride are used at an amount ranging from 2.0 to 4,0 equivalents and from 1.5 to 3.0 equivalents, respectively.

Following is a second method for preparing the compound of Formula I.

Initially, the 3-acetoxy-2-aryl propanol represented by Formula XIV is reacted with sulfamoyl chloride in an acetonitrile solvent in the presence of a base catalyst, to give the 3-acetoxy-2-aryl propanol sulfamate of Formula VI, as shown in Reaction Scheme IV:

Reaction Scheme IV

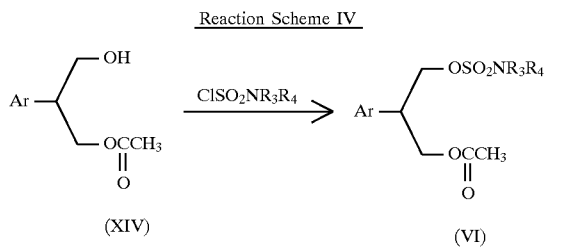

(XIV) (VI)

wherein Ar, $R_3$ and $R_4$ each are as defined above.

The 3-acetoxy-2-aryl propanol of Formula XIV is used at an amount of 0.1 to 2.0 moles. As the base catalyst, triethylamine, pyridine, antipyrin, or diisopropylethylamine is employed. Available reaction solvents include amide solvents, such as dimethylformamide, ethereal solvents, such as ethyl ether and tetrahydrofuran, and acetonitrile. Of them tetrahydrofuran and acetonitrile are preferred by virtue of their being easily removed after the reaction. It is preferable that this reaction is carried out at a temperature of −10° to 40° C. For example, if the reaction is executed at too low temperature, the reaction is very slow. On the other hand, if the reaction is carried out at a temperature higher than 40° C., the yield lowers by the production of unknown by-products. When considering reaction progress, convenience in after-treatment and economical aspects, it is preferable that the base catalyst and the sulfamoyl chloride are used at an amount ranging from 2.0 to 4.0 equivalents and from 1.5 to 3.0 equivalents, respectively, Thereafter, using a base catalyst, the 3-acetoxy-2-aryl propanol sulfamate represented by Formula VI is subjected to transesterification in an alcohol solvent, to give the 2-aryl-1,3-propandiol monosulfamate of Formula VII, as depicted in Reaction Scheme V:

Reaction Scheme V

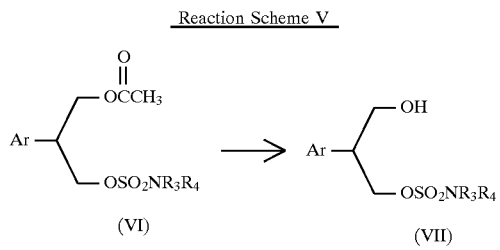

(VI) (VII)

wherein Ar, $R_3$ and $R_4$ each are as defined above.

In such transesterification, the 3-acetoxy-2-aryl propanol sulfamate of Formula VI is used at an amount of 0.1 to 2.0 moles. As the base catalyst, sodium hydroxide, potassium hydroxide, lithium hydroxide, sodium carbonate, sodium bicabonate, potassium carbonate, or potassium cyanide is used at an amount of 0.1 to 1.0 equivalent at a temperature of 0° to 30° C. Useful solvents include methylalcohol, ethylalcohol and propylalcohol. Preferred is methylalcohol when considering the reaction yield and the removal convenience after completion of the reaction. As the first method, the base catalyst remained in the reaction mixture is required to be inactivated after completion of the transesterification. For this, 1N hydrochloric acid solution or saturated ammonium chloride solution is preferably used.

In a subsequent procedure, the 2-aryl-1,3-1-propandiol monosulfamate of Formula VII obtained is reacted with carbonyldiimidazole in dichloromethane solvent to give the 3-imidazolyl carbonyloxy-2-arylpropanol sulfamate represented by formula XVII, which is, without purification, reacted with the substituted amine of Formula XVI to prepare the N,N'-substituted carbamoyl-2-aryl propanol sulfamate compounds of Formula I, the objective compound, as depicted in Reaction Scheme VI:

Reaction Scheme VI

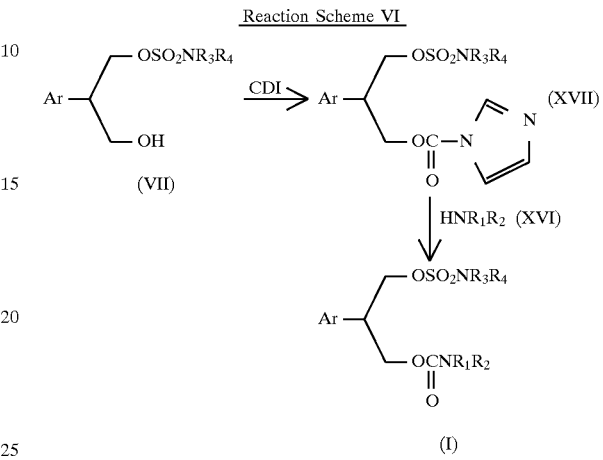

wherein Ar, $R_1$, $R_2$, $R_3$ and $R_4$ each are as defined above.

About 0.1 to 2.0 moles of the compound of Formula VII is preferably reacted with 1.1 to 2.5 equivalents of carbonyl diimidazole when considering yield and economical aspects. It is preferable that the former reaction of Reaction Scheme VI is carried out at a temperature of −5° to 40° C. For example, if the reaction is performed at a temperature less than −5° C., the reaction is very slow. On the other hand, if it is carried out at a temperature higher than 40° C., the yield decreases due to side reactions. Useful solvents for this reaction include low hydrocarbon halide solvents, such as methylene chloride and chloroform, ethereal solvents, such as ethyl ether and tetrahydrofuran, and acetonitrile with preference to methylene chloride, chloroform and tetrahydrofuran.

In the reaction of preparing the compound of Formula I from the compound of Formula XVII, the substituted amine is used at an amount of 1.0 to 5.0 equivalents at a temperature ranging from 0° to 30° C. in a solvent selected from tetrahydrofuran and methylene chloride.

In a third method for preparing the compound of Formula I, the 2-aryl-1,3-propandiol monosulfamate of Formula VII is reacted with isocyanate represented by Formula XVIII in a hydrocarbon halide or ethereal hydrocarbon solvent, to prepare the N,N'-substituted carbamoyl-2-aryl-1,3-propandiol sulfamate compound of Formula I, as shown in Reaction Scheme VII:

Reaction Scheme VII

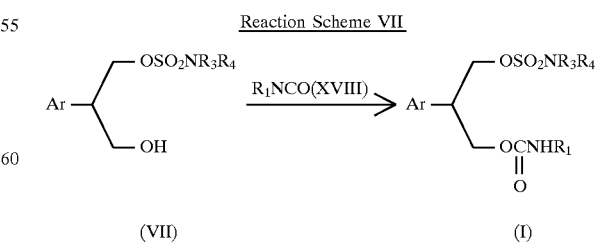

(VII) (I)

wherein Ar, $R_1$, $R_3$ and $R_4$ each are as defined above.

As shown in Reaction Scheme VII, the 2-aryl-1,3-propandiol monosulfamate of Formula VII, the starting material, is reacted preferably at an amount of about 0.1 to 2.0 moles with 1.0 to 2.0 equivalents of isocyanate when considering reaction progress and economical aspects. It is preferable that this reaction is carried out at a temperature of 0° to 80° C. For example, if the reaction is performed at a temperature less than 0° C., the reaction is not accomplished. On the other hand, if it is carried out at a temperature higher than 80° C., too much by-products are produced by the reaction of isocyanate itself. Useful solvents for this reaction include low hydrocarbon halide solvents, such as methylene chloride and chloroform, ethereal solvents, such as ethyl ether and tetrahydrofuran, and aromatic hydrocarbon solvents, such as benzene and toluene with preference to methylene chloride, chloroform, benzene and toluene.

In accordance with the present invention, the compound of Formula II is prepared by following pathway described below.

This preparation starts with (R)-3-acetoxy-2-aryl propanol as shown in Reaction Scheme VIII:

Reaction Scheme VIII

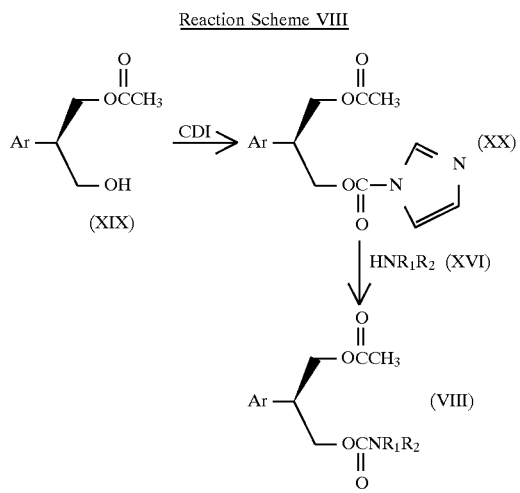

wherein Ar, $R_1$ and $R_2$ each are as defined above.

(R)-3-acetoxy-2-aryl propanol of Formula XIX is reacted with carbonyl diimidazole in dichloramethane solvent, to give (S)-3-imidazolyl carbonyloxy-2-aryl propanol acetate which is, without purification, reacted with the substituted amine of Formula XVI, to produce the (S)-3-N-substituted carbamoyl-2-aryl propanol acetate of Formula VIII.

The compound of Formula XIX, the starting material, is reacted preferably at an amount of about 0.1 to 2.0 moles with 1.1 to 2.5 equivalents of carbonyl diimidazole when considering yield and economical aspects. It is preferable that the former reaction of Reaction Scheme VIII is carried out at a temperature of −5° to 40° C. For example, if the reaction temperature is below −5° C. the reaction is very slow. On the other hand, if the former reaction is carried out at a temperature higher than 40° C., the yield decreases by side reactions. Useful solvents for this reaction include low hydrocarbon halide solvents, such as methylene chloride and chloroform, ethereal solvents, such as ethyl ether and tetrahydrofuran, and acetonitrile with preference to methylene chloride, chloroform and tetrahydrofuran.

For the preparation reaction of the compound of Formula VIII from the compound of Formula XX, the substituted amine is used at an amount of 1.0 to 5.0 equivalents. This reaction is executed at a temperature ranging from 0° to 30° C. in a solvent such as tetrahydrofuran and methylene chloride.

Then, the (S)-3-N-substituted carbamoyl-2-aryl propanol acetate of Formula VIII is subjected to transesterification to prepare (S)-3-N-substituted carbamoyl-2-aryl propanol of Formula IX in an alcohol solvent in the presence of a base catalyst, as shown in Reaction Scheme IX:

Reaction Scheme IX

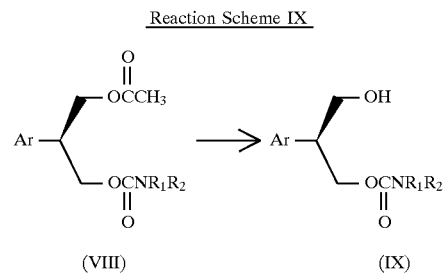

wherein Ar, $R_1$ and $R_2$ each are as defined above.

In the transesterification, the (S)-3-N-substituted carbamoyl-2-aryl propanol acetate of Formula VIII is used at an amount of 0.1 to 2.0 moles. As the base catalyst, sodium hydroxide, potassium hydroxide, lithium hydroxide, potassium carbonate, or potassium cyanide is used at an amount of 0.1 to 1.0 equivalent at a temperature of 0° to 30° C. Useful solvents include methylalcohol, ethylalcohol and propylalcohol. Preferred is methylalcohol when considering the reaction yield and the removal convenience after completion of the reaction.

Also, as mentioned in the first and the second methods for the preparation of the compounds of Formula I, it is needed that the base catalyst remained in the reaction mixture should be inactivated after the reaction. For this, 1N hydrochloric acid solution or saturated ammonium chloride solution is preferred.

In subsequence, the (S)-3-N-substituted carbamoyl-2-aryl propanol of Formula IX is reacted with sulfamoyl chloride in the presence of a base catalyst, to prepare the N,N'-substituted carbamoyl-2-aryl propanol sulfamate of Formula II. This reaction is depicted in Reaction Scheme X:

Reaction Scheme X

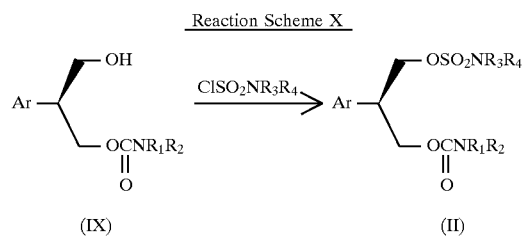

wherein Ar, $R_1$, $R_2$, $R_3$, and $R_4$ are as defined above.

The (S)-3-N-substituted carbamoyl-2-aryl propanol represented by Formula IX is used at an amount of 0.1 to 2.0 moles while the sulfamoyl chloride at an amount of about 1.0 to 3.0 equivalents. As the base catalyst, triethylamine, pyridine, antipyrin, or diisopropylethylamine is employed. When considering reaction progress, convenience in after-treatment and economical aspects, it is preferable that the base catalyst is used at an amount ranging from 2.0 to 4.0 equivalents. Available reaction solvents include amide solvents, such as dimethylformamide, ethereal solvents, such as ethyl ether and tetrahydrofuran, and acetonitrile with preference to tetrahydrofuran and acetonitrile. It is preferable that this reaction is carried out at a temperature of −10° to 40° C. For example, if the reaction temperature is maintained below −10° C., the reaction is significantly slow. On the other hand, if the reaction is carried out at a temperature higher than 40° C., the yield decreases by the production of unknown by-products.

There are two pathways for preparing the compound of Formula III, in accordance with the present invention.

In a first pathway, an (R)-3-acetoxy-2-aryl propanol of Formula (XIX) is used as the starting material, as shown in Reaction Scheme XI:

Reaction Scheme XI

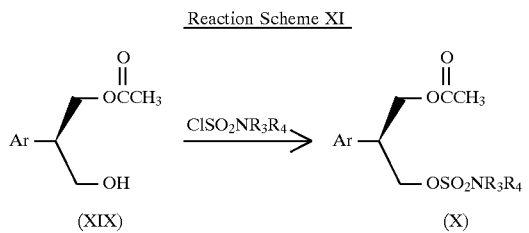

wherein Ar, $R_3$ and $R_4$ each are as defined above.

The (R)-3-acetoxy-2-aryl propanol of Formula XIX is reacted with sulfamoyl chloride in an acetonitrile solvent in the presence of a base catalyst, to give an (S)-3-acetoxy-2-aryl-1,3-propandiol sulfamate of Formula X.

The (R)-3-acetoxy-2-aryl propanol of Formula XIX is used at an amount of 0.1 to 2.0 moles. As the base catalyst, triethylamine, pyridine, antipyrin, or diisopropylethylamine is employed. When considering reaction progress, convenience in after-treatment and economical aspects, it is preferable that the base catalyst is used at an amount ranging from 2.0 to 4.0 equivalents. Available reaction solvents include amide solvents, such as dimethylformamide, ethereal solvents, such as ethyl ether and tetrahydrofuran, and acetonitrile. Of them tetrahydrofuran and acetonitrile are preferred.

It is preferable that this reaction is carried out at a temperature of $-10°$ to $40°$ C. For example, if the reaction is executed at too low temperature, the reaction is very slow. On the other hand, if the reaction is carried out at a temperature higher than $40°$ C., the yield decreases by the production of unknown by-products.

Thereafter, using a base catalyst, the (S)-3-acetoxy-2-aryl-1,3-propandiol sulfamate of Formula X is subjected to transesterification in an alcohol solvent, to give the (S)-2-aryl-1,3-propandiol monosulfamate of Formula XI, as depicted in Reaction Scheme XVI:

Reaction Scheme XVI

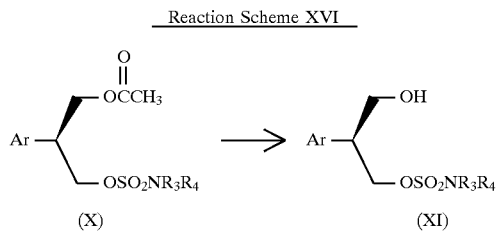

wherein Ar, $R_3$ and $R_4$ each are as defined above.

In this transesterification, the (S)-3-acetoxy-2-aryl-1,3-propandiol sulfamate of Formula X is used at an amount of about 0.1 to 2.0 moles, As the base catalyst, sodium hydroxide, potassium hydroxide, lithium hydroxide, potassium carbonate, or potassium cyanide is used at an amount of 0.1 to 1.0 equivalent at a temperature of $0°$ to $30°$ C. Useful solvents include methylalcohol, ethylalcohol and propylalcohol. Preferred is methylalcohol when considering the reaction yield and the removal convenience after completion of the reaction. As in the first method for the preparation of the compound of Formula I, the base catalyst remained in the reaction mixture is required to be inactivated after completion of the transesterification. For this, 1N hydrochloric acid solution or saturated ammonium chloride solution is preferably used.

There is a subsequent procedure in Reaction Scheme XIII:

Reaction Scheme XIII

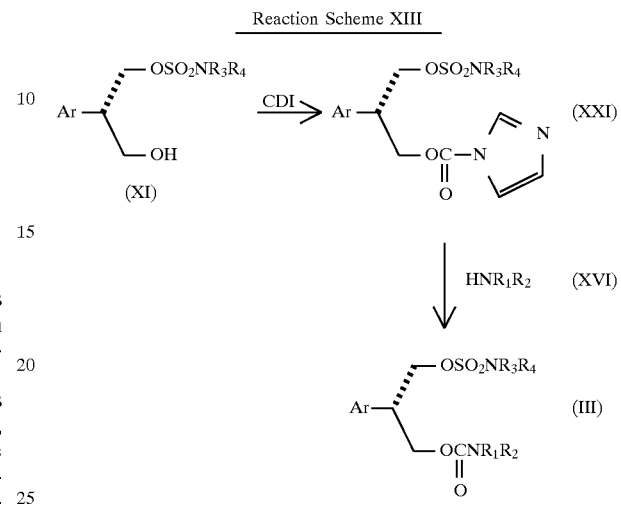

wherein Ar, $R_1$, $R_2$, $R_3$ and $R_4$ each are as defined above.

In Reaction Scheme XIII, the (S)-2-aryl-1,3-propandiol monosulfamate of Formula XI is reacted with carbonyl diimidazole in dichloromethane solvent to give the (S)-3-irnidazolyl carbonyloxy-2-arylpropanol sulfamate which is, without purification, with the substituted amine of Formula XVI, to prepare the N,N'-substituted carbamoyl-2-aryl propanol sulfamate of Formula III, the objective compound.

About 0.1 to 2.0 moles of the compound of Formula XI is preferably reacted with 1.1 to 2.5 equivalents of carbonyl diimidazole when considering yield and economical aspects. It is preferable that the former reaction of Reaction Scheme XIII is carried out at a temperature of $-5°$ to $40°$ C. For example, if the reaction is performed at a temperature less than $-5°$ C., the reaction is very slow. On the other hand, if it is carried out at a temperature higher than $40°$ C., the yield decreases by side reactions. Useful solvents for this reaction include low hydrocarbon halide solvents, such as methylene chloride and chloroform, ethereal solvents, such as ethyl ether and tetrahydrofuran, and acetonitrile with preference to methylene chloride, chloroform and tetrahydrofuran.

In the preparation reaction of the compound of Formula III from the compound of Formula XXI, the substituted amine is used at an amount of 1.0 to 5.0 equivalents at a temperature ranging from $0°$ to $30°$ C. in a solvent such as tetrahydrofuran and methylene chloride.

Alternatively, the compound of Formula III can be prepared by using (S)-3-acetoxy-2-aryl propanol of Formula XXII as the starting material, in accordance with the present invention, as shown in Reaction Scheme XIV:

Reaction Scheme XIV

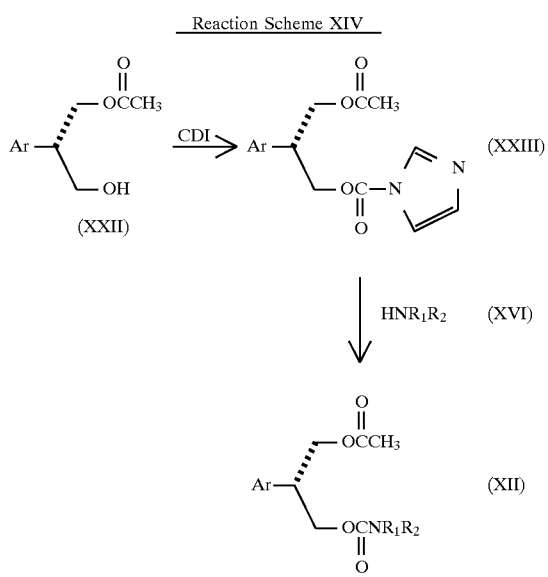

wherein Ar, $R_1$ and $R_2$ each are as defined above.

The (S)-3-acetoxy-2-aryl propanol of Formula XXII is reacted with carbonyl diimidazole in dichloromethane solution to give the (R)-3-imidazolyl carbonyloxy-2-aryl propanol acetate of Formula XXIII which is, without purification, reacted with the substituted amine of Formula XVI, to produce the (R)-3-N-substituted carbamoyl-2-aryl propanol acetate of Formula XII.

The compound of Formula XXII is reacted preferably at an amount of about 0.1 to 2.0 moles with 1.1 to 2.5 equivalents of carbonyl diimidazole when considering yield and economical aspects. It is preferable that the former reaction of Reaction Scheme XIV is carried out at a temperature of −5° to 40° C. For example, if the reaction is performed at a temperature less than −5° C., the reaction is very slow. On the other hand, if it is carried out at a temperature higher than 40° C., the yield decreases by side reactions. Useful solvents in this reaction include low hydrocarbon halide solvents, such as methylene chloride and chloroform, ethereal solvents, such as ethyl ether and tetrahydrofuran, and acetonitrile with preference to methylene chloride, chloroform and tetrahydrofuran.

The preparation reaction of the compound of Formula XII from the compound of Formula XXIII is carried out with 1.0 to 5.0 equivalents of the substituted amine at a temperature ranging from 0° to 30° C. in a solvent such as tetrahydrofuran and methylene chloride.

There is a subsequent procedure in Reaction Scheme XV:

Reaction Scheme XV

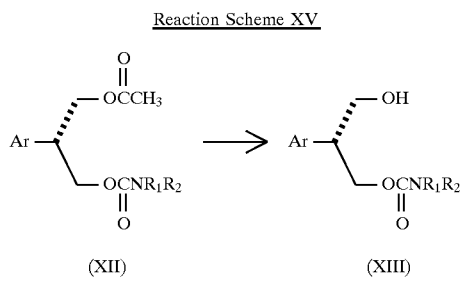

wherein Ar, $R_1$ and $R_2$ each are as defined above.

The (R)-3-N-substituted carbamoyl-2-aryl propanol acetate of Formula XII is subjected to transesterification to obtain the (R)-3-N-substituted carbamoyl-2-aryl propanol of Formula XIII. This reaction is executed in an alcohol solvent in the presence of a base catalyst.

In the transesterification, the (R)-3-N-substituted carbamoyl-2-aryl propanol acetate of Formula XII is used at an amount of 0.1 to 2.0 moles. As the base catalyst, sodium hydroxide, potassium hydroxide, lithium hydroxide, potassium carbonate, or potassium cyanide is used at an amount of 0.1 to 1.0 equivalent at a temperature of 0° to 30° C. Useful solvents include methylalcohol, ethylalcohol and propylalcohol. Preferred is methylalcohol when considering the reaction yield and the removal convenience after completion of the reaction. As in the first and the second methods for the preparation of the compound of Formula I, it is needed to inactivate the used base catalyst after the transesterification. For the inactivation of the base catalyst, 1N hydrochloric acid solution or saturated ammonium chloride solution is preferably used.

Next, the (R)-3-N-substituted carbamoyl-2-aryl propanol of Formula XIII is reacted with sulfamoyl chloride in the presence of a base catalyst, to prepare the objective compound of Formula III. This reaction is depicted in Reaction Scheme XVI:

Reaction Scheme XVI

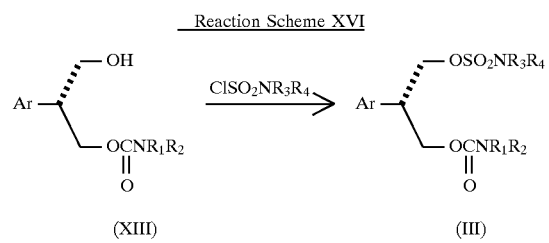

wherein Ar, $R_1$, $R_2$, $R_3$, and $R_4$, each are as defined above.

The (R)-3-N-substituted carbamoyl-2-aryl propanol represented by Formula XIII is used at an amount of 0.1 to 2.0 moles while sulfamoyl chloride at an amount of about 1.0 to 3.0 equivalents. As the base catalyst, triethylamine, pyridine, antipyrin, or diisopropylethylamine is employed. When considering reaction progress, convenience in after-treatment and economical aspects, it is preferable that the base catalyst is used at an amount ranging from 2.0 to 4.0 equivalents. Available reaction solvents include amide solvents, such as dimethylformamide, ethereal solvents, such as ethyl ether and tetrahydrofuran, and acetonitrile with preference to tetrahydrofuran and acetonitrile. It is preferable that this reaction is carried out at a temperature of −10° to 40° C. For example, if the reaction temperature is maintained below −10° C., the reaction is very slow. On the other hand, if the reaction is carried out at a temperature higher than 40° C., the yield decreases by the production of unknown by-products.

A better understanding of the present invention may be obtained in light of following examples which are set forth to illustrate, but are not to be construed to limit, the present invention.

EXAMPLE 1

Preparation of 3-Carbamoyl-2-phenyl propanol acetate

A well dried 1,000 ml flask equipped with a thermometer was purged with nitrogen gas, to completely take off moisture and air from the inside of the flask. This purging was continued for 30 min, after which 400 ml of purified methylene chloride was poured into the flask, 50 g of 3-acetoxy-2-phenyl propanol was well dissolved in the solvent and made to be homogeneous by stirring for 5 min. While being maintained at 0° C., the homogeneous solution was slowly added with 49.8 g of carbonyl diimidazole. After the starting material completely disappeared as measured by thin layer chromatography, 43.8 ml of aqueous ammonia was slowly added to the reaction solution in order to progress the reaction.

To determine when the reaction would be terminated, the reaction was under double monitoring of thin layer chromatography and liquid chromatography. Roughly, it took about 1 hour to finish the reaction.

After completion of reaction, 400 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (2:1) as a mobile phase, to obtain 58.0 g of 3-carbamoyl-2-phenyl propanol acetate as a white solid.

Yield 95%

H-NMR(CDCl$_3$, 200 MHz), ppm ($\delta$): 1.98(3H,s), 3.28 (1H,q), 4.28(4H,d), 5.21(2H,br), 7.27(5H,m).

EXAMPLE 2

Preparation of 3-N-methylcarbomoyl-2-phenyl propanol acetate

Except for using methylamine instead of aqueous ammonia, the same procedure with that of Example 1 was repeated.

A concentrated reaction mixture thus obtained was separated by column chromatography using a mixture of ethyl acetate/n-hexane (2:1) as a mobile phase, to obtain 58.9 g of 3-N-methylcarbomoyl-2-phenyl propanol acetate as a colorless liquid.

Yield 91%

H-NMR(CDCl$_3$, 200 MHz), ppm ($\delta$): 1.95(3H,s), 2.75 (3H,d), 3.28(1H,q), 4.21(4H,d), 5.15(2H,br), 7.27(5H,m).

EXAMPLE 3

Preparation of 3-N,N'-dimethylcarbamoyl-2-phenyl propanol acetate

Except for using dimethylamine instead of aqueous ammonia, the same procedure with that of Example 1 was repeated.

A concentrated reaction mixture thus obtained was separated by column chromatography using a mixture of ethyl acetate/n-hexane (2:1) as a mobile phase, to obtain 63.5 g of 3-N,N'-dimethylcarbamoyl-2-phenyl propanol acetate as a colorless liquid.

Yield 93%

H-NMR(CDCl$_3$, 200 MHz), ppm ($\delta$): 1.97(3H,s), 2.78 (6H,d), 3,34(1H,q), 4.17(2H,d), 4.39(2H,d), 7.32(5H,m)

EXAMPLE 4

Preparation of 3-N-isopropyl carbamoyl-2-phenyl propanol acetate

Except for using isopropylamine instead of aqueous ammonia, the same procedure with that of Example 1 was repeated.

A concentrated reaction mixture thus obtained was separated by column chromatography using a mixture of ethyl acetate/n-hexane (2:1) as a mobile phase, to obtain 64.7 g of 3-N-isopropylcarbamoyl-2-phenyl propanol acetate as a colorless liquid.

Yield 90%

H-NMR(CDCl$_3$, 200 MHz), ppm ($\delta$): 1.11(6H,s), 1.90 (3H,s), 3.35(1H,m), 3.71(1H,br), 4.43(4H,d), 4.64(1H,br), 7.35(5H,m).

EXAMPLE 5

Preparation of 3-N-cyclopropyl carbamoyl-2-phenyl propanol acetate

Except for using cyclopropyl amine instead of aqueous ammonia, the same procedure with that of Example 1 was repeated.

A concentrated reaction mixture thus obtained was separated by column chromatography using a mixture of ethyl acetate/n-hexane (2:1) as a mobile phase, to obtain 67.8 g of 3-N-cyclopropyl carbamoyl-2-phenyl propanol acetate as a colorless liquid.

Yield 95%

H-NMR(CDCl$_3$, 200 MHz), ppm ($\delta$): 0.45–0.81(6H,m), 2.01(3H,s), 2.52(1H,br), 3.37(1H,q), 4.45(4H,d), 4.87(1H, br), 7.32(5H,m).

EXAMPLE 6

Preparation of 3-N-morphoryl carbamoyl-2-phenyl propanol acetate

Except for using morphorine instead of aqueous ammonia, the same procedure with that of Example 1 was repeated.

A concentrated reaction mixture thus obtained was separated by column chromatography using a mixture of ethyl acetate/n-hexane (2:1) as a mobile phase, to obtain 72.8 g of 3-N-morphorylcarbamoyl-2-phenyl propanol acetate as a colorless liquid.

Yield 92%

H-NMR(CDCl$_3$, 200 MHz), ppm ($\delta$): 2.00(3H,s), 3.25–3.73(9H,br), 4.31(4H,d), 7.27(5H,m).

EXAMPLE 7

Preparation of 3-N-methylcarbamoyl-2-(o-chlorophenyl)propanol acetate

A well dried 1,000 ml flask equipped with a thermometer was purged with nitrogen gas, to completely take off moisture and air from the inside of the flask. This purging was continued for 30 min, after which 400 ml of purified methylene chloride was poured into the flask. 58.9 g of 3-acetoxy-2-(o-chlorophenyl)propanol was well dissolved in the solvent and made to be homogeneous by stirring for 5 min. While being maintained at 0° C., the homogeneous solution was slowly added with 49.8 g of carbonyl diimidazole. After the starting material completely disappeared as measured by thin layer chromatography, 60 ml of an aqueous methylamine solution was slowly added to the reaction solution in order to progress the reaction.

To determine when the reaction would be terminated, the reaction was under double monitoring of thin layer chromatography and liquid chromatography. Roughly, it took about 1 hour to finish the reaction.

After completion of reaction, 400 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (2:1) as a mobile phase, to obtain 68.5 g of 3-N-methylcarbamoyl-2-(o-chlorophenyl)propanol acetate as a colorless liquid.

Yield 93%

H-NMR(CDCl$_3$, 200 MHz), ppm ($\delta$): 2.05(3H,s), 2.82(d, 3H), 3.32(1H,q), 4.15–4.27(4H,m), 5.32(1H,br), 7.23–7.45 (4H,m).

EXAMPLE 8

Preparation of 3-Carbamoyl-2-Phenyl Propanol

A well dried 1,000 ml flask equipped with a thermometer was purged with nitrogen gas, to completely take off moisture and air from the inside of the flask. This purging was continued for 30 min, after which 500 ml of methanol was poured into the flask, 71 g of 3-carbamoyl-2-phenyl propanol acetate prepared in Example 1 was well dissolved in the solvent and made to be homogeneous by stirring for 30 min. While being maintained at 0° C., the homogeneous solution was slowly added with 3.3 g of potassium cyanide. The resulting reaction mixture was heated to room temperature with stirring. To determine when the reaction would be terminated, the reaction was under double monitoring of thin layer chromatography and liquid chromatography. Roughly, it took about 2 hours to finish the reaction.

After completion of the reaction, 300 ml of saturated ammonium chloride solution was added. Then, using a rotary evaporator, unreacted methanol was completely removed from the reaction solution. 200 ml of distilled water and 500 ml of ethyl acetate were added for solvent extraction. The organic layer thus obtained was dried over anhydrous magnesium sulfate and distilled off the solvent by a rotary evaporator, to give a yellow liquid.

This liquid obtained was added with 300 ml of toluene and stored in a refrigerator for 24 hrs, to produce 51.5 g of 3-carbamoyl-2-phenyl propanol as a white solid.

Yield 88%

H-NMR(CDCl$_3$, 200 MHz), ppm ($\delta$): 2.58(1H,t), 3.11 (1H,q) 3.82(2H,d), 4.39(2H,d), 4.91(2H,br), 7.27(5H,m).

EXAMPLE 9

Preparation of 3-N-methylcarbamoyl-2-phenyl propanol

Except for using 3-N-methylcarbamoyl-2-phenyl propanol acetate, instead of 3-carbamoyl-2-phenyl propanol acetate, as the starting material, the same procedure with that of Example 8 was repeated.

A concentrated reaction mixture thus obtained was separated by column chromatography using a mixture of ethyl acetate/n-hexane (3:1) as a mobile phase, to obtain 58.3 g of 3-N-methylcarbamoyl-2-phenyl propanol as a white solid.

Yield 93%

H-NMR(DMSO, 200 MHz), ppm ($\delta$): 2.52(3H,d), 3.01 (1H,q), 3.61(2H,t), 4.18(2H,m), 4.75(1H,t), 6.89(1H,d), 7.28(5H,m).

EXAMPLE 10

Preparation of 3-N,N'-Dimethylcarbamoyl-2-phenyl

Except for using 3-N,N'-dimethylcarbamoyl-2-phenyl propanol acetate, instead of 3-carbamoyl-2-phenyl propanol acetate, as the starting material, the same procedure with that of Example 8 was repeated.

A concentrated reaction mixture thus obtained was separated by column chromatography using a mixture of ethyl acetate/n-hexane (1:1) as a mobile phase, to obtain 60.9 g of 3-N,N'-dimethylcarbamoyl-2-phenyl propanol as a colorless liquid.

Yield 91%

H-NMR(DMSO, 200 MHz), ppm ($\delta$): 2.61(6H,d), 3.10 (1H,q), 3.73(2H,d), 4.12(2H,d), 4.74(1H,t), 7.34(5H,m).

EXAMPLE 11

Preparation of 3-N-Isopropyl carbamoyl-2-phenyl propanol

Except for using 3-N-isopropyl carbamoyl-2-phenyl propanol acetate, instead of 3-carbamoyl-2-phenyl propanol acetate, as the starting material, the same procedure with that of Example 8 was repeated.

A concentrated reaction mixture thus obtained was separated by column chromatography using a mixture of ethyl acetate/n-hexane (1:1) as a mobile phase, to obtain 63.3 g of 3-N-isopropyl carbamoyl-2-phenyl propanol as a white solid.

Yield 89%

H-NMR(DMSO, 200 MHz), ppm ($\delta$): 1.00(6H,d), 2.52 (1H,d), 2.95(1H,t), 3.62(2H,d), 4.18(2H,m), 4.74(1H,t), 6.91(1H,d), 7.28(5H,m).

EXAMPLE 12

Preparation of 3-N-cyclopropyl carbamoyl-2-phenyl propanol

Except for using 3-N-cyclopropyl carbamoyl-2-phenyl propanol acetate, instead of 3-carbamoyl-2-phenyl propanol acetate, as the starting material, the same procedure with that of Example 8 was repeated.

A concentrated reaction mixture thus obtained was separated by column chromatography using a mixture of ethyl acetate/n-hexane (1:1) as a mobile phase, to obtain 65.6 g of 3-N-cyclopropyl carbamoyl-2-phenyl propanol acetate as a white solid.

Yield 93%

H-NMR(DMSO, 200 MHz), ppm ($\delta$): 0.35–0.55(4H,m), 2.52(1H,s), 3.01(1H,t), 3.6(2H,d), 4.25(2H,m), 4.76(1H,t), 7.14(1H,d), 7.28(5H,m).

EXAMPLE 13

Preparation of 4-N-Morphoryl carbamoyl-2-phenyl propanol

Except for using 3-N-morphoryl carbamoyl-2-phenyl propanol acetate, instead of 3-carbamoyl-2-phenyl propanol acetate, as the starting material, the same procedure with that of Example 8 was repeated.

A concentrated reaction mixture thus obtained was separated by column chromatography using a mixture of ethyl acetate/n-hexane (3:1) as a mobile phase, to obtain 71.4 g of 3-N-morphorylcarbamoyl-2-phenyl propanol as a white solid.

Yield 90%

H-NMR(DMSO, 200 MHz), ppm($\delta$): 2.82(1H,br), 3.15 (1H,q), 3.27–3.60(8H,br), 3.79(2H,d), 4.35(2H,d), 7.25(5H, m).

EXAMPLE 14

Preparation of 3-N-methylcarbamoyl-2-(o-chlorophenyl)propanol

A well dried 1,000 ml flask equipped with a thermometer was purged with nitrogen gas, to completely take off moisture and air from the inside of the flask. This purging was continued for 30 min, after which 500 ml of methanol was poured into the flask. 85.7 g of 3-N-methylcarbamoyl-2-(o-chlorophenyl)propanol acetate prepared in Example 7 was well dissolved in the solvent and made to be homogeneous by stirring for 30 min. While being maintained at 0° C., the homogeneous solution was slowly added with 3.3 g of potassium cyanide. The resulting reaction mixture was heated to room temperature with stirring. To determine when the reaction would be terminated, the reaction was under double monitoring of thin layer chromatography and liquid chromatography. Roughly, it took about 2 hours to finish the reaction.

After completion of the reaction, 300 ml of saturated ammonium chloride solution was added. Then, using a rotary evaporator, unreacted methanol was completely removed from the reaction solution. 200 ml of distilled water and 500 ml of ethyl acetate were added for solvent extraction. The organic layer thus obtained was dried over anhydrous magnesium sulfate and distilled off the solvent by a rotary evaporator, to give a yellow liquid.

This liquid obtained was added with 500 ml of toluene and stored in a refrigerator for 24 hrs, to produce 65.8 g of 3-N-methylcarbamoyl-2-(o-chlorophenyl)propanol as a white solid.

Yield 90%

H-NMR(CDCl$_3$, 200 MHz), ppm ($\delta$): 2.48(3H,d), 2.56 (1H,t), 3.13(1H,q), 3.87–4.12(4H,br), 5.60(1H,br), 7.25–7.42(4H,m).

EXAMPLE 15

Preparation of 3-Carbamoyl-2-phenyl propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 97.5 g of 3-carbamoyl-2-phenyl propanol prepared in Example 8 and 121.3 ml of pyridine were well dissolved in the solvent and made to be homogeneous by stirring for 30 min, While being maintained at 0° C., the homogeneous solution was slowly added with 115.5 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, unreacted acetonitrite was completely removed from the reaction solution using a rotary evaporator. Then, 600 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was added with 500 ml of ethyl ether and stored in a refrigerator for 24 hrs, to produce 116.5 g of 3-carbamoyl-2-phenyl propanol sulfamates a white solid.

Yield 85%

H-NMR(DMSO, 200 MHz), ppm ($\delta$): 3.35(1H,q), 4.16 (2H,d), 4.34(2H,d), 6.57(2H,br), 7.39(5H,s), 7.58(2H,s).

EXAMPLE 16

Preparation of 3-N-Methylcarbamoyl-2-phenyl propanol sulfamate

Except for using 3-N-Methylcarbomoyl-2-phenyl propanol, instead of 3-carbamoyl-2-phenyl propanol as the starting material, the same procedure with that of Example 15 was repeated.

A concentrated reaction mixture thus obtained was added with 500 ml of ethyl ether and stored in a refrigerator for 24 hrs, to produce 126.7 g of 3-N-methylcarbamoyl-2-phenyl propanol sulfamate as a white solid.

Yield 88%

H-NMR(DMSO, 200 MHz), ppm($\delta$): 2.54(3H,d), 3.35 (1H,q), 4.29(4H,m), 6.98(1H,br), 7.29(5H,s), 7.53(2H,s).

EXAMPLE 17

Preparation of 3-N,N'-Dimethylcarbamoyl-2-phenyl propanol sulfamate

Except for using 3-N,N'-dimethylcarbamoyl-2-phenyl propanol, instead of 3-carbamoyl-2-phenyl propanol, as the starting material, the same procedure with that of Example 15 was repeated.

A concentrated reaction mixture thus obtained was added with 500 ml of ethyl ether and stored in a refrigerator for 24 hrs, to produce 125.3 g of 3-N,N'-dimethylcarbamoyl-2-phenyl propanol sulfamate as a white solid.

Yield 83%

H-NMR(CDCl$_3$, 200 MHz), ppm($\delta$): 2.84(6H,d), 3.38 (1H,q), 4.39(4H,m), 4.93(2H,s), 7.21(5H,d).

EXAMPLE 18

Preparation of 3-N-Isopropyl carbamoyl-2-phenyl propanol sulfamate

Except for using 3-N-isopropyl carbamoyl-2-phenyl propanol, instead of 3-carbamoyl-2-phenyl propanol, as the starting material, the same procedure with that of Example 15 was repeated.

A concentrated reaction mixture thus obtained was added with 500 ml of ethylether and stored in a refrigerator for 24 hrs, to produce 134.3 g of 3-N-isopropyl carbamoyl-2-phenyl propanol sulfamate as a white solid.

Yield 85%

H-NMR(DMSO, 200 MHz), ppm($\delta$): 1.01(6H,m), 3.32 (1H,m), 3.55(1H,q), 4.18(2H,d), 4.29(2.H,d), 6.95(1H,d), 7.34(5H,s), 7.56(2H,s).

EXAMPLE 19

Preparation of 3-N-Cyclopropyl carbamoyl-2-phenyl propanol sulfamate

Except for using 3-N-cyclopropyl carbamoyl-2-phenyl propanol, instead of 3-carbamoyl-2-phenyl propanol, as the starting material, the same procedure with that of Example 15 was repeated.

A concentrated reaction mixture thus obtained was added with 500 ml of ethylether and stored in a refrigerator for 24 hrs, to produce 135.0 g of 3-N-cyclopropyl carbamoyl-2-phenyl propanol sulfamate as a white solid.

Yield 86%

H-NMR(DMSO, 200 MHz), ppm($\delta$): 0.35–0.58(4H,m), 2.51(1H,s), 3.35(1H,q), 4.15–4.36(4H,m), 7.15(1H,br), 7.29 (5H,s), 7.52(2H,s).

EXAMPLE 20

Preparation of 3-N-Morphoryl carbamoyl-2-phenyl propanol sulfamate

Except for using 3-N-morphoryl carbamoyl-2-phenyl propanol, instead of 3-carbamoyl-2-phenyl propanol, as the starting material, the same procedure with that of Example 15 was repeated.

The liquid thus obtained was added with 500 ml of ethylether and stored in a refrigerator for 24 hrs, to produce 163.6 g of 3-N-morphorylcarbamoyl-2-phenyl propanol sulfamate as a white solid.

Yield 95%

H-NMR(CDCl$_3$, 200 MHz) ppm($\delta$): 3.05(1H,q), 3.20–3.50(8H,br), 4.15(4H,m), 4.43(2H,s), 7.13(5H,m).

EXAMPLE 21

Preparation of 3-N-Methylcarbamoyl-2-(o-chlorophenyl)propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 121.8 g of 3-N-methylcarbamoyl-2-(o-chlorophenyl)propanol prepared in Example 14 and 121.3 ml of pyridine were well dissolved in the solvent and made to be homogeneous by stirring for 30 min. While being maintained at 0° C., the homogeneous solution was slowly added with 113.5 g of sulfamoyl chloride (prepared in the method described in Chem. Ber. 91, 1339–1241 (1958), to Appel and Berger). At the same temperature, the reaction was proceeded and its progress was monitored by thin layer chromatography and liquid chromatography. Roughly, it took about 2 hours to finish the reaction.

After completion c)f the reaction, acetonitrile was completely removed from the reaction mixture by using a rotary evaporator, 600 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was added with 500 ml of ethylether and stored in a refrigerator for 24 hrs, to produce 143.6 g of 3-N-methylcarbamoyl-2-(o-chlorophenyl)propanol sulfamate as a white solid.

Yield 89%

H-NMR(DMSO, 200 MHz), ppm ($\delta$): 2.53(3H,d), 3.32 (1H,q), 4.33(4H,m), 6.53(1H,br), 7.35(4H,m), 7.62(2H,s).

EXAMPLE 22

Preparation of 3-Acetoxy-2-phenyl-1,3-propandiol sulfamate

A well dried 1,000 ml flask equipped with a thermometer was purged with nitrogen gas, to completely take off moisture and air from the inside of the flask. This purging was continued for 30 min, after which 300 ml of purified acetonitrile was poured into the flask. 50 g of 3-acetoxy-2-phenyl propanol and 61 ml of pyridine were well dissolved in the solvent and made to be homogeneous by stirring for 30 min. While being maintained at 0° C., the homogeneous solution was slowly added with 59.6 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, acetonitrile was completely removed from the reaction solution using a rotary evaporator. Then, 300 ml of distilled water and 300 ml of ethyl acetate were added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to produce 60.1 g of 3-acetoxy-2-phenyl-1,3-propandiol sulfamate as a white solid.

Yield 87%

H-NMR(DMSO, 200 MHz), ppm($\delta$): 1.95(3H,s), 3.36 (1H,q), 4.28(4H,d), 7.28(5H,s), 7.53(2H,s).

EXAMPLE 23

Preparation of 2-Phenyl-1,3-propandiol monosulfamate

A well dried 1,000 ml flask equipped with a thermometer was purged with nitrogen gas, to completely take off moisture and air from the inside of the flask. This purging was continued for 30 min, after which 500 ml of methanol was poured into the flask. 27.3 g of 3-acetoxy-2-phenyl-1,3-propandiol sulfamate prepared in Example 22 was well dissolved in the solvent and made to be homogeneous by stirring for 30 min. While being maintained at 0° C., the homogeneous solution was slowly added with 3.3 g of potassium cyanide. The resulting reaction mixture was heated to room temperature with stirring. To determine when the reaction would be terminated, the reaction was under double monitoring of thin layer chromatography and liquid chromatography. Roughly, it took about 1 hours to finish the reaction.

After completion of the reaction, 50 ml of saturated ammonium chloride solution was added. Then, using a rotary evaporator, unreacted methanol was completely removed from the reaction solution. 200 ml of distilled water and 200 ml of ethyl acetate were added for solvent extraction. The organic layer thus obtained was dried over anhydrous magnesium sulfate and distilled off the solvent by a rotary evaporator, to give a yellow solid.

This solid was washed with 50 ml of methylene chloride and purified to produce 19 g of 2-phenyl-1,3-propandiol monosulfamate.

Yield 81%

H-NMR(DMSO, 200 MHz), ppm($\delta$): 3.12(1H,q), 3.61 (2H,d), 4.24(2H,m), 4.86(1H,t), 7.15(5H,m), 7.46(2H,s).

EXAMPLE 24

Preparation of 3-N-Methylcarbamoyl-2-phenyl propanol sulfamate

A well dried 1,000 ml flask equipped with a thermometer was purged with nitrogen gas, to completely take off moisture and air from the inside of the flask. This purging was continued for 30 min, after which 300 ml of purified methylene chloride was poured into the flask. 23.3 g of 2-phenyl-1,3-propandiol monosulfamate prepared in Example 23 was well dissolved in the solvent and made to be homogeneous by stirring for 30 min. While being maintained at 0° C., the homogeneous solution was slowly added with 19.4 g of carbonyl diimidazole. The resulting reaction mixture was slowly heated to room temperature with stirring. To determine when the reaction would be terminated, the reaction was under double monitoring of thin layer chromatography and liquid chromatography. Roughly, it took about 15 min to finish the reaction. After the starting material completely disappeared, 47 ml of methyl amine aqueous solution was slowly introduced through a syringe with stirring at room temperature. It took about 2 hours to completely terminate this reaction.

Then, using a rotary evaporator, the solvent remaining was completely removed from the reaction solution. 200 ml of distilled water and 200 ml of ethyl acetate were added for solvent extraction. The organic layer thus obtained was dried over anhydrous magnesium sulfate and distilled off the solvent by a rotary evaporators to give a yellow liquid.

This solid was washed with 150 ml of ethyl ether and stored in a refrigerator for 24 hrs, to produce 24.4 g of 3-N-methylcarbamoyl-2-phenyl propanol sulfamate.

Yield 85%

H-NMR(DMSO, 200 MHz), ppm($\delta$): 2.54(3H, d), 3.35 (1H,q), 4.29(4H,m), 6.89(1H,br), 7.29(5H,s), 7.53(2H,s).

EXAMPLE 25

Preparation of 3-Carbamoyl-2-phenyl propanol sulfamate

Except for using aqueous ammonia instead of methylamine, the same procedure with that of Example 24 was repeated.

A liquid obtained was added with 150 ml of ethyl ether and stored in a refrigerator for 24 hrs to produce 27.0 g of 3-carbamoyl-2-phenyl propanol sulfamate as a white solid.

Yield 80%

H-NMR(DMSO, 200 MHz), ppm ($\delta$): 3.35(1H,q), 4.16 (2H,d), 4.34(2H,d), 6.57(2H,br), 7.39(5H,s), 7.58(2H,s), 1.98(3H,s), 3.28(1H,q).

EXAMPLE 26

Preparation of 3-N,N'-Dimethylcarbamoyl-2-phenyl propanol sulfamate

Except for using dimethylamine instead of methylamine, the same procedure with that of Example 24 was repeated.

A liquid obtained was added with 150 ml of ethylether and stored in a refrigerator for 24 hrs, to produce 27.0 g of 3-N,N'-dimethylcarbamoyl-2-phenyl propanol sulfamate as a white solid.

Yield 80%

H-NMR(DMSO, 200 MHz), ppm($\delta$): 2.84(6H,d), 3.38 (1H,q), 4.39(4H,m), 4.93(2H,s), 7.21(5H,d).

EXAMPLE 27

Preparation of 3-N-Isopropyl carbamoyl-2-phenyl propanol sulfamate

Except for using isopropyl amine instead of methyl amine the same procedure with that of Example 24 was repeated.

A liquid obtained was added with 150 ml of ethylether and stored in a refrigerator for 24 hrs, to produce 26.0 g of 3-N-isopropyl carbamoyl-2-phenyl propanol sulfamate.

Yield 82%

H-NMR(DMSO, 200 MHz), ppm($\delta$): 1.01(6H,m), 3.32 (1H,m), 3.55(1H,q), 4.18(2H,d), 4.29(2H,d), 6.95(1H,d), 7.34(5H,s).

EXAMPLE 28

Preparation of 3-N-Cyclopropyl carbamoyl-2-phenyl propanol sulfamate

Except for using cyclopropyl amine instead of methyl amine, the same procedure with that of Example 24 was repeated.

A liquid obtained was added with 150 ml of ethylether and stored in a refrigerator for 24 hrs, to produce 27.6 g of 3-N-cyclopropyl carbamoyl-2-phenyl propanol sulfamate.

Yield 88%

H-NMR(DMSO, 200 MHz) ppm($\delta$): 0.35–0.58(4H,m), 2.51(1H,s), 3.35(1H,q), 4.16–4.36(4H,m), 7.15(1H,br), 7.29 (5H,s).

EXAMPLE 29

Preparation of 3-N-Morphoryl carbamoyl-2-phenyl propanol sulfamate

Except for using morphorine instead of methyl amine, the same procedure with that of Example 24 was repeated.

A liquid thus obtained was added with 500 ml of ethylether and stored in a refrigerator for 24 hrs, to produce 32 g of 3-N-morphorylcarbamoyl-2-phenyl propanol sulfamate.

Yield 93%

H-NMR(DMSO, 200 MHz) ppm($\delta$): 3.05(1H,q) 3.20–3.50(8H,br), 4.15(4H,m), 4.43(2H,s), 7.13(5H,m).

EXAMPLE 30

Preparation of 3-N-Phenyl carbamoyl-2-phenyl propanol sulfamate

A well dried 1,000 ml flask equipped with a thermometer and a condenser was purged with nitrogen gas, to completely take off moisture and air from the inside of the flask. This purging was continued for 30 min, after which 300 ml of purified dichloromethane was poured into the flask. 23.3 g of 2-phenyl-1,3-propandiol monosulfamate prepared in Example 20 was well dissolved in the solvent and made to be homogeneous by stirring for 30 min. While being maintained at room temperature, the homogeneous solution was slowly added with 14.3 g of phenylisocyanate. The resulting solution was slowly heated into 40° C. with stirring, in order to progress the reaction.

To determine when the reaction would be terminated, the reaction was under double monitoring of thin layer chromatography and liquid chromatography. Roughly, it took about 6 hours to finish the reaction.

After completion of reaction, dichloromethane remaining was removed from the solution by use of a rotary evaporator. 100 ml of distilled water and 100 ml of ethyl acetate was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n- hexane (1:1) as a mobile phase, to obtain 24.5 g of 3-N-phenyl carbamoyl-2-phenyl propanol sulfamate.

Yield 70%

H-NMR(CDCl$_3$, 200 MHz), ppm(δ): 3.46(1H,m), 4.41 (4H,m), 5.05(2H,br), 7.05(1H,br), 7.31(10H,m).

EXAMPLE 31

Preparation of (S)-3-Carbamoyl-2-phenyl propanol acetate

A well dried 1,000 ml flask equipped with a thermometer was purged with nitrogen gas, to completely take off moisture and air from the inside of the flask. This purging was continued for 30 min, after which 500 ml of purified methylene chloride was poured into the flask. 50 g of (R)-3-acetoxy-2-phenyl propanol was well dissolved in the solvent and made to be homogeneous by stirring for 5 min. While being maintained at 0° C., the homogeneous solution was slowly added with 49.8 g of carbonyl diimidazole. After the starting material completely disappeared as measured by thin layer chromatography, 43.8 ml of aqueous ammonia was slowly added to the reaction solution in order to progress the reaction.

To determine when the reaction would be terminated, the reaction was under double monitoring of thin layer chromatography and liquid chromatography. Roughly, it took about 2 hours to finish the reaction.

After completion of reaction, 500 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to obtain 56.2 g of (S)-3-carbamoyl-2-phenyl propanol acetate.

Yield 92%

H-NMR(DMSO, 200 MHz), ppm(δ): 1.98(3H,s), 3.28 (1H,q), 4.28(4H,d), 5.21(2H,br), 7.27(5H,m).

EXAMPLE 32

Preparation of (S)-3-N-methylcarbamoyl-2-phenyl propanol acetate

Except for using methylamine instead of aqueous ammonia, the same procedure with that of Example 31 was repeated.

A concentrated reaction mixture thus obtained was separated by column chromatography using a mixture of ethyl acetate/n-hexane (1:1) as a mobile phase, to obtain 58.2 g of (S)-3-N-methylcarbamoyl-2-phenyl propanol acetate as a colorless liquid.

Yield 90%

H-NMR(CDCl$_3$, 200 MHz), ppm(δ): 1.95(3H,s), 2.75 (3H,d), 3.28(1H,q), 4.21(4H,d), 5.15(1H,br), 7.27(5H,m).

EXAMPLE 33

Preparation of (S)-3-N,N'-dimethylcarbamoyl-2-phenyl propanol acetate

Except for using dimethylamine instead of aqueous ammonia, the same procedure with that of Example 31 was repeated.

A concentrated reaction mixture thus obtained was separated by column chromatography using a mixture of ethyl acetate/n-hexane (1:1) as a mobile phase, to obtain 62.8 g of (S)-3-N,N'-dimethylcarbamoyl-2-phenyl propanol acetate as a colorless liquid.

Yield 92%

H-NMR(CDCl$_3$, 200 MHz), ppm(δ): 1.97(3H,s), 2.78 (6H,d), 3.34(1H,q), 4.17(2H,d), 4.39(2H,d), 7.32(5H,m).

EXAMPLE 34

Preparation of (S)-3-N-isopropyl carbamoyl-2-phenyl propanol acetate

Except for using isopropyl amine instead of aqueous ammonia, the same procedure with that of Example 31 was repeated.

A concentrated reaction mixture thus obtained was separated by column chromatography using a mixture of ethyl acetate/n-hexane (1:1) as a mobile phase, to obtain 66.9 g of (S)-3-N-isopropylcarbamoyl-2-phenyl propanol acetate as a colorless liquid.

Yield 93%

H-NMR(CDCl$_3$, 200 MHz), ppm(δ): 1.11(6H,m), 1.90 (3H,s), 3.35(1H,m), 3.71(1H,br), 4.43(4H,d), 4.64(1H,br), 7.35(5H,m).

EXAMPLE 35

Preparation of (S)-3-N-cyclopropyl carbamoyl-2-phenyl propanol acetate

Except for using cyclopropyl amine instead of aqueous ammonia, the same procedure with that of Example 31 was repeated.

A concentrated reaction mixture thus obtained was separated by column chromatography using a mixture of ethyl acetate/n-hexane (1:1) as a mobile phase, to obtain 64.2 g of (S)-3-N-cyclopropyl carbamoyl-2-phenyl propanol acetate as a colorless liquid.

Yield 90%

H-NMR(CDCl$_3$, 200 MHz), ppm(δ): 0.45–0.81(6H,m), 2.01(3H,s), 2.52(1H,br), 3.37(1H,q), 4.45(4H,d), 4.87(1H, br), 7.32(5H,m).

EXAMPLE 36

Preparation of (S)-3-N-morphoryl carbamoyl-2-phenyl propanol acetate

Except for using morphorine instead of aqueous ammonia, the same procedure with that of Example 31 was repeated.

A concentrated reaction mixture thus obtained was separated by column chromatography using a mixture of ethyl acetate/n-hexane (1:1) as a mobile phase, to obtain 75.2 g of (S)-3-N-morphorylcarbamoyl-2-phenyl propanol acetate as a colorless liquid.

Yield 95%

H-NMR(CDCl$_3$, 200 MHz) ppm(δ): 2.00(3H,s), 3.25–3.73(9H,br), 4.31(4H,d), 7.27(5H,m).

EXAMPLE 37

Preparation of (S)-3-N-methylcarbamoyl-2-(m-chlorophenyl)propanol acetate

A well dried 1,000 ml flask equipped with a thermometer was purged with nitrogen gas, to completely take off moisture and air from the inside of the flask. This purging was continued for 30 min, after which 500 ml of purified methylene chloride was poured into the flask. 58.9 g of (R)-3-acetoxy-2-(m-chlorophenyl)propanol was well dissolved in the solvent and made to be homogeneous by stirring for 5 min. While being maintained at 0°0 C., the homogeneous solution was slowly added with 49.8 g of carbonyl diimidazole. After the starting material completely disappeared as measured by thin layer chromatography, 60 ml of an aqueous methylamine solution was slowly added to the reaction solution in order to progress the reaction.

To determine when the reaction would be terminated, the reaction was under double monitoring of thin layer chromatography and liquid chromatography. Roughly, it took about 2 hours to finish the reaction.

After completion of reaction, 500 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to obtain 71.2 g of (S)-3-N-methylcarbamoyl-2-(m-chlorophenyl)propanol acetate.

Yield 90%

H-NMR(DMSO, 200 MHz), ppm($\delta$): 2.12(3H,s), 2.90(d, 3H), 3.31(1H,q), 4.12–4.31(4H,m), 5.52(1H,br), 7.28–7.41 (4H,m).

EXAMPLE 38

Preparation of (S)-3-Carbamoyl-2-phenyl propanol

A well dried 1,000 ml flask equipped with a thermometer was purged with nitrogen gas, to completely take off moisture and air from the inside of the flask. This purging was continued for 30 min, after which 500 ml of methanol was poured into the flask. 47.4 g of (S)-3-carbamoyl-2-phenyl propanol acetate prepared in Example 31 was well dissolved in the solvent and made to be homogeneous by stirring for 30 min. While being maintained at 0° C., the homogeneous solution was slowly added with 3.9 g of potassium cyanide. The resulting reaction mixture was heated to room temperature with stirring. To determine when the reaction would be terminated, the reaction was under double monitoring of thin layer chromatography and liquid chromatography. Roughly, it took about 2 hours to finish the reaction.

After completion of the reaction, 200 ml of saturated ammonium chloride solution was added. Then, using a rotary evaporator, unreacted methanol was completely removed from the reaction solution. 200 ml of distilled water and 400 ml of ethyl acetate were added for solvent extraction. The organic layer thus obtained was dried over anhydrous magnesium sulfate and distilled off the solvent by a rotary evaporator, to give a yellow liquid.

This liquid obtained was added with 200 ml of toluene and stored in a refrigerator for 24 hrs, to produce 35.5 g of (S)-3-carbamoyl-2-phenyl propanol as a white solid.

Yield 91%

H-NMR(CDCl$_3$, 200 MHz), ppm($\delta$): 2.58(1H,t), 3.11(1H, q), 3.82(2H,d), 4.39(2H,d), 4.91(2H,br), 7.27(5H,m)

EXAMPLE 39

Preparation of (S)-3-N-methylcarbamoyl-2-phenyl propanol

Except for using (S)-3-N-methylcarbamoyl-2-phenyl propanol acetate, instead of (S)-3-carbamoyl-2-phenyl propanol acetate, as the starting material, the same procedure with that of Example 38 was repeated.

A concentrated reaction mixture thus obtained was separated by column chromatography using a mixture of ethyl acetate/n-hexane (1:1) as a mobile phase, to obtain 37.2 g of (S)-3-N-methylcarbamoyl-2-phenyl propanol as a white solid.

Yield 89%

H-NMR(DMSO, 200 MHz), ppm($\delta$): 2.52(3H,d), 3.01 (1H,q), 3.61(2H,t), 4.18(2H,m), 4.75(1H,t), 6.98(1H,d), 7.28(5H,m).

EXAMPLE 40

Preparation of (S)-3-N,N'-Dimethylcarbamoyl-2-phenyl propanol

Except for using (S)-3-N,N'-dimethylcarbamoyl-2-phenyl propanol acetate, instead of (S)-3-carbamoyl-2-phenyl propanol acetate, as the starting material, the same procedure with that of Example 38 was repeated.

A concentrated reaction mixture thus obtained was separated by column chromatography by using a mixture of ethyl acetate/n-hexane (1:1) as a mobile phase, to obtain 38.8 g of (S)-3-N,N'-dimethylcarbamoyl-2-phenyl propanol as a colorless liquid.

Yield 87%

H-NMR(DMSO, 200 MHz), ppm($\delta$): 2.61(6H,d), 3.10 (1H,q), 3.73(2H,d), 4.12(2H,m), 4.74(1H,t), 7.34(5H,m).

EXAMPLE 41

Preparation of (S)-3-N-Isopropyl carbamoyl-2-phenyl propanol

Except for using (S)-3-N-isopropyl carbamoyl-2-phenyl propanol acetate, instead of (S)-3-carbamoyl-2-phenyl propanol acetate, as the starting material, the same procedure with that of Example 38 was repeated.

A concentrated reaction mixture thus obtained was separated by column chromatography using a mixture of ethyl acetate/n-hexane (1:1) as a mobile phase, to obtain 41.7 g of (S)-3-N-isopropyl carbamoyl-2-phenyl propanol as a white solid.

Yield 88%

H-NMR(DMSO, 200 MHz), ppm($\delta$): 1.00(6H,d), 2.52 (1H,d), 2.95(1H,t), 3.62(2H,d), 4.18(2H,m), 4.74(1H,t), 6.91(1H,d), 7.28(5H,m).

EXAMPLE 42

Preparation of (S)-3-N-Cyclopropyl carbamoyl-2-phenyl propanol

Except for using (S)-3-N-cyclopropyl carbamoyl-2-phenyl propanol acetate, instead of (S)-3-carbamoyl-2-phenyl propanol acetate, as the starting material, the same procedure with that of Example 38 was repeated.

A concentrated reaction mixture thus obtained was separated by column chromatography using a mixture of ethyl acetate/n-hexane (1:1) as a mobile phase, to obtain 42.8 g of (S)-3-N-cyclopropyl carbamoyl-2-phenyl propanol as a white solid.

Yield 91%

H-NMR(DMSO, 200 MHz), ppm($\delta$): 0.35–0.55(4H,m), 2.52(1H,s), 3.01(1H,t), 3.61(2H,d), 4.25(2H,m), 4.76(1H,t), 7.14(1H,d), 7.28(5H,m).

EXAMPLE 43

Preparation of (S)-3-N-Morphoryl carbamoyl-2-phenyl propanol

Except for using (S)-3-N-morphoryl carbamoyl-2-phenyl propanol acetate, instead of (S)-3-carbamoyl-2-phenyl propanol acetate as the starting material, the same procedure with that of Example 38 was repeated.

A concentrated reaction mixture thus obtained was separated by column chromatography using a mixture of ethyl acetate/n-hexane (1:1) as a mobile phase, to obtain 47.2 g of (S)-3-N-morphorylcarbamoyl-2-phenyl propanol as a white solid.

Yield 89%

H-NMR(DMSO, 200 MHz), ppm($\delta$): 2.82(1H,br), 3.15 (1H,q) 3.27–3.60(8H,br), 3.79(2H,d), 4.35(2H,d), 7.25(5H, m).

EXAMPLE 44

Preparation of (S)-3-N-Methylcarbamoyl-2-(m-chlorophenyl)propanol

A well dried 1,000 ml flask equipped with a thermometer was purged with nitrogen gas, to completely take off moisture and air from the inside of the flask. This purging was continued for 30 min, after which 500 ml of methanol was poured into the flask. 69.5 g of (S)-3-N-methylcarbamoyl-2-(m-chlorophenyl)propanol acetate prepared in Example 37 was well dissolved in the solvent and made to be homogeneous by stirring for 30 min. While being maintained at 0° C., the homogeneous solution was slowly added with 3.9 g of potassium cyanide. The resulting reaction mixture was heated to room temperature with stirring. To determine when the reaction would be terminated, the reaction was under double monitoring of thin layer chromatography and liquid chromatography. Roughly, it took about 2 hours to finish the reaction.

After completion of the reaction, 200 ml of saturated ammonium chloride solution was added. Then, using a rotary evaporator, unreacted methanol was completely removed from the reaction solution. 200 ml of distilled water and 400 ml of ethyl acetate were added for solvent extraction. The organic layer thus obtained was dried over anhydrous magnesium sulfate and distilled off the solvent by a rotary evaporator, to give a yellow liquid.

This liquid obtained was added with 300 ml of toluene and stored in a refrigerator for 24 hrs, to produce 50.5 g of (S)-3-N-methylcarbamoyl-2-(m-chlorophenyl)propanol as a white solid.

Yield 85%

H-NMR(CDCl$_3$, 200 MHz), ppm($\delta$): 2.41(3H,d), 2.51 (1H,t), 3.20(1H,q), 3.92–4.15(4H,br), 5.58(1H,br), 7.30–7.49(4H,m).

EXAMPLE 45

Preparation of (R)-3-Carbamoyl-2-phenyl propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 58.5 g of (S)-3-carbamoyl-2-phenyl propanol prepared in Example 38 and 156.8 ml of diisopropyl ethylamine were well dissolved in the solvent and made to be homogeneous by stirring for 30 min. While being maintained at 0° C., the homogeneous solution was slowly added with 69.3 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, unreacted acetonitrile was completely removed from the reaction solution using a rotary evaporator. Then, 600 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was separated by column chromatography using a mixture of ethyl acetate/n-hexane (1:1) as a mobile phase, to obtain 73.2 g of (R)-3-carbamoyl-2-phenyl propanol sulfamates a white solid.

Yield 89%

H-NMR(DMSO, 200 MHz), ppm($\delta$): 3.35(1H,q), 4.16 (2H,d), 4.34(2H,d), 6.57(2H,br), 7.39(5H,s), 7.58(2H,s).

EXAMPLE 46

Preparation of (R)-3-N-Methylcarbamoyl-2-phenyl propanol sulfamate

Except for using (S)-3-N-methylcarbamoyl-2-phenyl propanol, instead of (S)-3-carbamoyl-2-phenyl propanol, as the starting material, the same procedure with that of Example 45 was repeated.

A concentrated reaction mixture thus obtained was separated by column chromatography using a mixture of ethyl acetate/n-hexane (1:I) as a mobile phase, to obtain 76.9 g of (R)-3-N-methylcarbamoyl-2-phenyl propanol sulfamate as a white solid.

Yield 89%

H-NMR(DMSO, 200 MHz), ppm($\delta$): 2.54(3H,d), 3.35 (1H,q), 4.29(4H,m), 6.98(1H,br), 7.29(5H,s), 7.53(2H,s).

EXAMPLE 47

Preparation of (R)-3-N,N'-Dimethylcarbamoyl-2-phenyl propanol sulfamate

Except for using (S)-3-N,N'-dimethylcarbamoyl-2-phenyl propanol, instead of (S)-3-carbamoyl-2-phenyl propanol, as the starting material, the same procedure with that of Example 45 was repeated.

A concentrated reaction mixture thus obtained was separated by column chromatography using a mixture of ethyl acetate/n-hexane (1:1) as a mobile phase, to obtain 77.9 g of (R)-3-N,N'-dimethylcarbamoyl-2-phenyl propanol sulfamate as a white solid.

Yield 86%

H-NMR(CDCl$_3$, 200 MHz), ppm($\delta$): 2.84(6H,d), 3.38 (1H,q), 4.39(4H,m), 4.93(2H,s), 7.21(5H,d).

EXAMPLE 48

Preparation of (R)-3-N-Isopropyl carbamoyl-2-phenyl propanol sulfamate

Except for using (S)-3-N-isopropyl carbamoyl-2-phenyl propanol, instead of (S)-3-carbamoyl-2-phenyl propanol, as the starting material, the same procedure with that of Example 45 was repeated.

A concentrated reaction mixture thus obtained was separated by column chromatography using a mixture of ethyl acetate/n-hexane (1:1) as a mobile phase, to obtain 79.6 g of (R)-3-N-isopropyl carbamoyl-2-phenyl propanol sulfamate as a white solid.

Yield 84%

H-NMR(DMSO, 200 MHz), ppm($\delta$): 1.01(6H,m), 3.32 (1H,m), 3.55(1H,q), 4.18(2H,d), 4.29(2H,d), 6.95(1H,d), 7.34(5H,s), 7.56(2H,s).

EXAMPLE 49

Preparation of (R)-3-N-Cyclopropyl carbamoyl-2-phenyl propanol sulfamate

Except for using (S)-3-N-cyclopropyl carbamoyl-2-phenyl propanol, instead of (S)-3-carbamoyl-2-phenyl propanol, as the starting material, the same procedure with that of Example 45 was repeated.

A concentrated reaction mixture thus obtained was separated by column chromatography using a mixture of ethyl acetate/n-hexane (1:1) as a mobile phase, to produce 84.8 g of (R)-3-N-cyclopropyl carbamoyl-2-phenyl propanol sulfamate as a white solid.

Yield 90%

H-NMR(DMSO, 200 MHz) ppm($\delta$): 0.35–0.58(4H,m), 2.51(1H,s), 3.35(1H,q), 4.16–4.36(4H,m), 7.15(1H,br), 7.29 (5H,s), 7.52(2H,s).

EXAMPLE 50

Preparation of (R)-3-N-Morphoryl carbamoyl-2-phenyl propanol sulfamate

Except for using (S)-3-N-morphoryl carbamoyl-2-phenyl propanol, instead of (S)-3-carbamoyl-2-phenyl propanol, as the starting material, the same procedure with that of Example 45 was repeated.

The liquid thus obtained was separated by column chromatography using a mixture of ethyl acetate/n-hexane (11) as a mobile phase, to produce 87.8 g of (R)-3-N-morphorylcarbamoyl-2-phenyl propanol sulfamate as a white solid.

Yield 85%

H-NMR(DMSO, 200 MHz) ppm($\delta$): 3.05(1H,q), 3.20–3.50(8H,br), 4.15(4H,m), 4.43(2H,s), 7.13(5H,m).

EXAMPLE 51

Preparation of (R)-3-N-Methylcarbamoyl-2-(m-chlorophenyl)propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 73.1 g of (S)-3-N-methylcarbamoyl-2-(m-chlorophenyl)propanol prepared in Example 44 and 156.8 ml of diisopropyl ethylamine were well dissolved in the solvent and made to be homogeneous by stirring for 30 min. While being maintained at 0° C., the homogeneous solution was slowly added with 69.3 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours Lo finish the reaction.

After completion of the reaction, acetonitrile remaining was completely removed from the reaction mixture by using a rotary evaporator. 600 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was separated by column chromatography using a mixture of ethyl acetate/n-hexane (1:1) as a mobile phase, to produce 73.2 g of (R)-3-N-methylcarbamoyl-2-(m-chlorophenyl)propanol sulfamate as a white solid.

Yield 89%

H-NMR(DMSO, 200 MHz), ppm ($\delta$): 2.50(3H,d), 3.35 (1H,q), 4.28(4H,m), 6.52(1H,br), 7.38(4H,m), 7.56(2H,s).

EXAMPLE 52

Preparation of (S)-3-Acetoxy-2-phenyl-1,3-propandiol sulfamate

A well dried 1,000 ml flask equipped with a thermometer was purged with nitrogen gas, to completely take off moisture and air from the inside of the flask. This purging was continued for 30 min, after which 300 ml of purified acetonitrile was poured into the flask. 50 g of (R)-3-acetoxy-2-phenyl propanol and 61 ml of pyridine were well dissolved in the solvent and made to be homogeneous by stirring for 30 min, While being maintained at 0° C., the homogeneous solution was slowly added with 59.6 g of sulfamoyl chloride (prepared in the method described in Chem. Ber,, 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, acetonitrile was completely removed from the reaction solution using a rotary evaporator. Then, 300 ml of distilled water and 300 ml of ethyl acetate were added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to produce 61.3 g of (S)-3-acetoxy-2-phenyl-1,3-propandiol sulfamate as a white solid.

Yield 88%

H-NMR(DMSO, 200 MHz), ppm($\delta$): 1.95(3H,s), 3.36 (1H,q), 4.28(4H,d), 7.28(5H,s), 7.53(2H,s).

EXAMPLE 53

Preparation of (S)-2-Phenyl-1,3-propandiol monosulfamate

A well dried 1,000 ml flask equipped with a thermometer was purged with nitrogen gas, to completely take off moisture and air from the inside of the flask. This purging was continued for 30 min, after which 500 ml of methanol was poured into the flask. 27.3 g of (S)-3-acetoxy-2-phenyl-3-propandiol sulfamate prepared in Example 52 was well dissolved in the solvent and made to be homogeneous by stirring for 30 min. While being maintained at 0° C., the homogeneous solution was slowly added with 3.3 g of potassium cyanide. The resulting reaction mixture was heated to room temperature with stirring. To determine when the reaction would be terminated, the reaction was under double monitoring of thin layer chromatography and liquid chromatography. Roughly, it took about 4 hours to finish the reaction.

After completion of the reaction, 50 ml of saturated ammonium chloride solution was added. Then, using a rotary evaporator, unreacted methanol was completely removed from the reaction solution. 200 ml of distilled water and 200 ml of ethyl acetate were added for solvent extraction. The organic layer thus obtained was dried over anhydrous magnesium sulfate and distilled off the solvent by a rotary evaporator, to give a yellow solid.

This solid was washed with 50 ml of methylene chloride and filtered to produce 19 g of (S)-2-phenyl-1,3-propandiol monosulfamate as a white solid.

Yield 81%

H-NMR(DMSO, 200 MHz), ppm($\delta$): 3.12(1H,q), 3.61 (2H,d), 4.24(2H,m), 4.86(1H,t), 7.15(5H,m), 7.46(2H,s).

EXAMPLE 54

Preparation of (S)-3-N-Methylcarbamoyl-2-phenyl propanol sulfamate

A well dried 1,000 ml flask equipped with a thermometer was purged with nitrogen gas, to completely take off moisture and air from the inside of the flask. This purging was continued for 30 min, after which 300 ml of purified methylene chloride was poured into the flask. 23.3 g of (S)-2-phenyl-1,3-propandiol monosulfamate prepared in Example 53 was well dissolved in the solvent and made to be homogeneous by stirring for 30 min. While being maintained at 0° C., the homogeneous solution was slowly added with 19.4 g of carbonyl diimidazole. The resulting reaction mixture was slowly heated to room temperature with stirring. To determine when the reaction would be terminated, the reaction was under double monitoring of thin layer chromatography and liquid chromatography. Roughly, it took about 15 mins to finish the reaction. After the starting material completely disappeared, 47 ml of methyl amine aqueous solution was slowly introduced through a syringe with stirring at room temperature. It took about 2 hours to completely terminate this reaction.

Then, using a rotary evaporator, the solvent remaining was completely removed from the reaction solution. 200 ml of distilled water and 200 ml of ethyl acetate were added for solvent extraction. The organic layer thus obtained was dried over anhydrous magnesium sulfate and distilled off the solvent by a rotary evaporator, to give a yellow liquid.

This liquid was added with 150 ml of ethyl ether and stored in a refrigerator for 24 hrs, to produce 24.4 g of (S)-3-N-methylcarbomoyl-2-phenyl propanol sulfamate, Yield 85%

H-NMR(DMSO, 200 MHz), ppm($\delta$): 2.54(3H,d), 3.35 (1H,q), 4.29(4H,m), 6.98(1H,br), 7.29(5H,s), 7.53(2H,s)

EXAMPLE 55

Preparation of (S)-3-Carbamoyl-2-phenyl propanol sulfamate

Except for using aqueous ammonia instead of methylamine, the same procedure with that of Example 54 was repeated.

A liquid obtained was added with 150 ml of ethyl ether and stored in a refrigerator to produce 27.0 g of (S)-3-carbamoyl-2-phenyl propanol sulfamate as a white solid.

Yield 80%

H-NMR(DMSO, 200 MHz), ppm($\delta$): 3.35(1H,q), 4.16 (2H,d), 4.34(2H,d), 6.57(2H,br), 7.39(5H,s), 7.58(2H,s), 1.98(3H,s), 3.28(1H,q).

EXAMPLE 56

Preparation of (S)-3-N,N'-Dimethylcarbamoyl-2-phenyl propanol sulfamate

Except for using dimethylamine instead of methylamine, the same procedure with that of Example 54 was repeated.

A liquid obtained was added with 150 ml of ethylether and stored in a refrigerator for 24 hrs, to produce 27.0 g of (S)-3-N,N'-dimethylcarbamoyl-2-phenyl propanol sulfamate as a white solid.

Yield 80%

H-NMR(DMSO, 200 MHz), ppm($\delta$): 2.84(6H,d), 3.38 (1H,q), 4.39(4H,m), 4.93(2H,s), 7.21(5H,d).

EXAMPLE 57

Preparation of (S)-3-N-Isopropyl carbamoyl-2-phenyl propanol sulfamate

Except for using isopropyl amine instead of methyl amine the same procedure with that of Example 54 was repeated.

A liquid obtained was added with 150 ml of ethylether and stored in a refrigerator for 24 hrs, to produce 26.0 g of (S)-3-N-isopropyl carbamoyl-2-phenyl propanol sulfamate.

Yield 82%

H-NMR(DMSO, 200 MHz), ppm($\delta$): 1.01(6H,m), 3.32 (1H,m), 3.55(1H,q), 4.18(2H,d), 4.29(2H,d), 6.95(1H,d), 7.34(5H,s).

EXAMPLE 58

Preparation of (S)-3-N-Cyclopropyl carbamoyl-2-phenyl propanol sulfamate

Except for using cyclopropyl amine instead of methyl amine, the same procedure with that of Example 54 was repeated.

A liquid obtained was added with 150 ml of ethylether and stored in a refrigerator for 24 hrs, to produce 27.6 g of (S)-3-N-cyclopropyl carbamoyl-2-phenyl propanol sulfamate.

Yield 88%

H-NMR(DMSO, 200 MHz) ppm($\delta$): 0.35–0.58(4H,m), 2.51(1H,s), 3.35(1H,q), 4.16–4.36(4H,m), 7.15(1H,br), 7.29 (5H,s).

EXAMPLE 59

Preparation of (S)-3-N-Morphoryl carbamoyl-2-phenyl propanol sulfamate

Except for using morphorine instead of methyl amine, the same procedure with that of Example 54 was repeated.

A liquid thus obtained was added with 500 ml of ethylether and stored in a refrigerator for 24 hrs, to produce 33 g of (S)-3-N-morphoryl carbamoyl-2-phenyl propanol sulfamate.

Yield 96%

H-NMR(DMSO, 200 MHz) ppm(δ): 3.05(1H,q), 3.20–3.50(8H,br), 4.15(4H,m), 4.43(2H,s), 7.13(5H,m).

EXAMPLE 60

Preparation of (R)-3-Carbamoyl-2-phenyl propanol acetate

A well dried 1,000 ml flask equipped with a thermometer was purged with nitrogen gas, to completely take off moisture and air from the inside of the flask. This purging was continued for 30 min, after which 500 ml of purified methylene chloride was poured into the flask. 50 g of (S)-3-acetoxy-2-phenyl propanol was well dissolved in the solvent and made to be homogeneous by stirring for 5 min. While being maintained at 0° C., the homogeneous solution was slowly added with 49.8 g of carbonyl diimidazole. After the starting material completely disappeared as measured by thin layer chromatography, 43.8 ml of aqueous ammonia was slowly added to the reaction solution in order to progress the reaction.

To determine when the reaction would be terminated, the reaction was under double monitering of thin layer chromatography and liquid chromatography. Roughly, it took about 2 hours to finish the reaction.

After completion of reaction, 500 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to obtain 55 g of (R)-3-carbamoyl-2-phenyl propanol acetate.

Yield 90%

H-NMR(DMSO, 200 MHz), ppm(δ): 1.98(3H,s), 3.28 (1H,q), 4.28(4H,d), 5.21(2H,br), 7.27(5H,m).

EXAMPLE 61

Preparation of (R)-3-N-methylcarbamoyl-2-phenyl propanol acetate

Except for using methylamine instead of aqueous ammonia, the same procedure with that of Example 60 was repeated.

A concentrated reaction mixture thus obtained was separated by column chromatography using a mixture of ethyl acetate/n-hexane (1:1) as a mobile phase, to obtain 62.1 g of (R)-3-N-methylcarbamoyl-2-phenyl propanol acetate as a colorless liquid.

Yield 96%

H-NMR(CDCl$_3$, 200 MHz), ppm(δ): 1.95(3H,s), 2.5(3H, d), 3.28(1H,q), 4.21(4H,d), 5.15(1H,br), 7.27(5H,m).

EXAMPLE 62

Preparation of (R)-3-N,N'-dimethylcarbamoyl-2-phenyl propanol acetate

Except for using dimethylamine instead of aqueous ammonia, the same procedure with that of Example 60 was repeated.

A concentrated reaction mixture thus obtained was separated by column chromatography using a mixture of ethyl acetate/n-hexane (1:1) as a mobile phase, to obtain 61.4 g of (R)-3-N,N'-dimethylcarbamoyl-2-phenyl propanol acetate is a colorless liquid.

Yield 90%

H-NMR(CDCl$_3$, 200 MHz), ppm(δ): 1.97(3H,s), 2.78 (6H,d), 3.34(1H,q), 4.17(2H,d), 4.39(2H,d), 7.32(5H,m).

EXAMPLE 63

Preparation of (R)-3-N-isopropyl carbamoyl-2-phenyl propanol acetate

Except for using isopropyl amine instead of aqueous ammonia, the same procedure with that of Example 60 was repeated.

A concentrated reaction mixture thus obtained was separated by column chromratography using a mixture of ethyl acetate/n-hexane (1:1) as a mobile phase, to obtain 66.3 g of (R)-3-N-cyclopropyl carbomoyl-2-phenyl propanol acetate as a colorless liquid.

Yield 91%

H-NMR(CDCl$_3$, 200 MHz), ppm(δ): 1.11(6H,m), 1.90 (3H,s), 3.35(1H,m), 3.71(1H,br), 4.43(4H,d), 4.64(1H,br), 7.35(5H,m).

EXAMPLE 64

Preparation of (R)-3-N-cyclopropyl carbamoyl-2-phenyl propanol acetate

Except for using cyclopropyl amine instead of aqueous ammonia, the same procedure with that of Example 60 was repeated.

A concentrated reaction mixture thus obtained was separated by column chromatography using a mixture of ethyl acetate/n-hexane (1:1) as a mobile phase, to obtain 66.3 g of (R)-3-N-cyclopropyl carbamoyl-2-phenyl propanol acetate as a colorless liquid.

Yield 93%

H-NMR(CDCl$_3$, 200 MHz), ppm(δ): 0.45–0.81(6H,m), 2.01(3H,s), 2.52(1H,br), 3.37(1H,q), 4.45(4H,d), 4.87(1H, br), 7.32(5H,m).

EXAMPLE 65

Preparation of (R)-3-N-morphoryl carbamoyl-2-phenyl propanol acetate

Except for using morphorine instead of aqueous ammonia, the same procedure with that of Example 60 was repeated, A concentrated reaction mixture thus obtained was separated by column chromatography using a mixture of ethyl acetate/n-hexane (1:1) as a mobile phase, to obtain 70.5 g of (R)-3-N-morphorylcarbamoyl-2-phenyl propanol acetate as a colorless liquid.

Yield 89%

H-NMR(CDCl$_3$, 200 MHz), ppm(δ): 2.00(3H,s), 3.25–3.73(9H,br), 4.31(4H,d), 7.27(5H,m).

EXAMPLE 66

Preparation of (R)-3-N-methylcarbamoyl-2-(p-methoxyphenyl)propanol acetate

A well dried 1,000 ml flask equipped with a thermometer was purged with nitrogen gas, to completely take off moisture and air from the inside of the flask. This purging was continued for 30 min, after which 500 ml of purified methylene chloride was poured into the flask. 57.8 g of (S)-3-acetoxy-2-(p-methoxyphenyl)propanol was well dissolved in the solvent and made to be homogeneous by stirring for 5 min. While being maintained at 0° C., the homogeneous solution was slowly added with 49.8 g of carbonyl diimidazole. After the starting material completely disappeared as measured by thin layer chromatography, 60 ml of an aqueous methylamine solution was slowly added to the reaction solution in order to progress the reaction.

To determine when the reaction would be terminated, the reaction was under double monitering of thin layer chromatography and liquid chrormatography. Roughly, it took about 2 hours to finish the reaction.

After completion of reaction, 500 ml of distilled water was added for solvent extraction. The organic layer thus obtained was dried over anhydrous magnesium sulfate and distilled off the solvent by a rotary evaporator, to give a yellow liquid.

This concentrated liquid mixture was separated by column chromatography using a mixture of ethyl acetate/n-hexane (1:1) as a mobile phase, to obtain 69.6 g of (R)-3-N-methylcarbamoyl-2-(p-methoxyphenyl)propanol acetate.

Yield 96%

H-NMR(DMSO, 200 MHz), ppm($\delta$): 2.12(3H,s), 2.85(d, 3H), 3.25(1H,q), 4.20–4.32(4H,m), 5.24(1H,br), 6.89(2H, d), 7.23(2H,d).

EXAMPLE 67

Preparation of (R)-3-Carbamoyl-2-phenyl propanol

A well dried 1,000 ml flask equipped with a thermometer was purged with nitrogen gas, to completely take off moisture and air from the inside of the flask. This purging was continued for 30 min, after which 500 ml of methanol was poured into the flask. 47.4 g of (R)-3-carbamoyl-2-phenyl propanol acetate prepared in Example 60 was well dissolved in the solvent and made to be homogeneous by stirring for 30 min. While being maintained at 0° C., the homogeneous solution was slowly added with 3.9 g of potassium cyanide. The resulting reaction mixture was heated to room temperature with stirring. To determine when the reaction would be terminated, the reaction was under double monitering of thin layer chromatography and liquid chromatography. Roughly, it took about 2 hours to finish the reaction.

After completion of the reaction, 200 ml of saturated ammonium chloride solution was added. Then, using a rotary evaporator, unreacted methanol was completely removed from the reaction solution. 200 ml of distilled water and 400 ml of ethyl acetate were added for solvent extraction. The organic layer thus obtained was dried over anhydrous magnesium sulfate and distilled off the solvent by a rotary evaporator, to give a yellow liquid.

This liquid obtained was added with 200 ml of toluene and stored in a refrigerator for 24 hrs, to produce 36.7 g of (R)-3-carbamoyl-2-phenyl propanol as a white solid.

Yield 94%

H-NMR(CDCl$_3$, 200 MHz), ppm($\delta$): 2.58(1H,t), 3.11(1H, q) 3.82(2H,d), 4.39(2H,d), 4.91(2H,br), 7.27(5H,m).

EXAMPLE 68

Preparation of (R)-3-N-methylcarbamoyl-2-phenyl propanol

Except for using (R)-3-N-methylcarbamoyl-2-phenyl propanol acetate, instead of (R)-3-carbamoyl-2-phenyl propanol acetate, as the starting material, the same procedure with that of Example 67 was repeated.

A concentrated reaction mixture thus obtained was separated by column chromatography using a mixture of ethyl acetate/n-hexane (1:1) as a mobile phase, to obtain 38.9 g of (R)-3-N-methylcarbamoyl-2-phenyl propanol as a white solid.

Yield 93%

H-NMR(DMSO, 200 MHz), ppm($\delta$): 2.52(3H,d), 3.01 (1H,q), 3.61(2H,t), 4.18(2H,m), 4.75(1H,t), 6.98(1H,d), 7.28(5H,m).

EXAMPLE 69

Preparation of (R)-3-N,N'-Dimethylcarbamoyl-2-phenyl propanol

Except for using (R)-3-N,N'-dimethylcarbamoyl-2-phenyl propanol acetate, instead of (R)-3-carbamoyl-2-phenyl propanol acetate, as the starting material, the same procedure with that of Example 67 was repeated.

A concentrated reaction mixture thus obtained was separated by column chromatography using a mixture of ethyl acetate/n-hexane (1:1) as a mobile phase, to obtain 41.5 g of (R)-3-N,N'-dimethylcarbamoyl-2-phenyl propanol as a colorless liquid.

Yield 93%

H-NMR(DMSO, 200 MHz), ppm($\delta$): 2.61(6H,d), 3.10 (1H,q), 3.73(2H,d), 4.12(2H,m), 4.74(1H,t), 7.34(5H,m).

EXAMPLE 70

Preparation of (R)-3-N-Isopropyl carbamoyl-2-phenyl propanol

Except for using (R)-3-N-isopropyl carbamoyl-2-phenyl propanol acetate, instead of (R)-3-carbamoyl-2-phenyl propanol acetate, as the starting material, the same procedure with that of Example 67 was repeated.

A concentrated reaction mixture thus obtained was separated by column chromatography using a mixture of ethyl acetate/n-hexane (1:1) as a mobile phase, to obtain 42.6 g of (R)-3-N-isopropyl carbamoyl-2-phenyl propanol as a white solid.

Yield 90%

H-NMR(DMSO, 200 MHz), ppm($\delta$): 1.00(6H,d), 2.52 (1H,d), 2.95(1H,t), 3.62(2H,d), 4.18(2H,m), 4.74(1H,t), 6.91(1H,d), 7.28(5H,m).

EXAMPLE 71

Preparation of (R)-3-N-Cyclopropyl carbamoyl-2-phenyl propanol

Except for using (R)-3-N-cyclopropyl carbamoyl-2-phenyl propanol acetate, instead of (R)-3-carbamoyl-2-phenyl propanol acetate, as the starting material, the same procedure with that of Example 67 was repeated.

A concentrated reaction mixture thus obtained was separated by column chromatography using a mixture of ethyl acetate/n-hexane (1:1) as a mobile phase, to obtain 44.2 g of (R)-3-N-cyclopropyl carbamoyl-2-phenyl propanol as a white solid.

Yield 94%

H-NMR(DMSO, 200 MHz), ppm($\delta$): 0.35–0.55(4H,m), 2.52(1H,s), 3.01(1H,t), 3.61(2H,d), 4.25(2H,m), 4.76(1H,t), 7.14(1H,d), 7.28(5H,m).

EXAMPLE 72

Preparation of (R)-3-N-Morphoryl carbamoyl-2-phenyl propanol

Except for using (R)-3-N-morphoryl carbamoyl-2-phenyl propanol acetate, instead of (R)-3-carbamoyl-2-phenyl propanol acetate, as the starting material, the same procedure with that of Example 67 was repeated.

A concentrated reaction mixture thus obtained was separated by column chromatography using a mixture of ethyl acetate/n-hexane (1:1) as a mobile phase, to obtain 48.3 g of (R)-3-N-morphorylcarbamoyl-2-phenyl propanol as a white solid.

Yield 91%

H-NMR(DMSO, 200 MHz), ppm($\delta$): 2.82(1H,br), 3.15 (1H,q), 3.27–3.60(8H,br), 3.79(2H,d), 4.35(2H,d), 7.25(5H, m).

EXAMPLE 73

Preparation of (R)-3-N-Methylcarbamoyl-2-(p-methoxyphenyl)propanol

A well dried 1,000 ml flask equipped with a thermometer was purged with nitrogen gas, to completely take off moisture and air from the inside of the flask. This purging was continued for 30 min, after which 500 ml of methanol was poured into the flask. 56.3 g of (R)-3-N-methylcarbamoyl-2-(p-methoxyphenyl)propanol acetate prepared in Example 66 was well dissolved in the solvent and made to be homogeneous by stirring for 30 min. While being maintained at 0° C., the homogeneous solution was slowly added with 3.9 g of potassium cyanide. The resulting reaction mixture was heated to room temperature with stirring. To determine when the reaction would be terminated, the reaction was under double monitering of thin layer chromatography and liquid chromatography. Roughly, it look about 2 hours to finish the reaction.

After completion of the reaction, 200 ml of saturated ammonium chloride solution was added. Then, using a rotary evaporator, unreacted methanol was completely removed from the reaction solution. 200 ml of distilled water and 400 ml of ethyl acetate were added for solvent extraction. The organic layer thus obtained was dried over anhydrous magnesium sulfate and distilled off the solvent by a rotary evaporator, to give a yellow liquid.

This liquid obtained was added with 100 ml of toluene and stored in a refrigerator for 24 hrs, to produce 40.7 g of (R)-3-N-methylcarbamoyl-2-(p-methoxyphenyl)propanol as a white solid.

Yield 85%

H-NMR(CDCl$_3$, 200 MHz), ppm($\delta$): 2.39(3H,d), 2.51 (1H,t), 3.24(1H,q), 3.75–4.05(4H,br), 5.43(1H,br), 6.91(2H, d), 7.20(2H,d).

EXAMPLE 74

Preparation of (S)-3-Carbamoyl-2-phenyl propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 58.5 g of (R)-3-carbamoyl-2-phenyl propanol prepared in Example 67 and 156.8 ml of diisopropyl ethylamine were well dissolved in the solvent and made to be homogeneous by stirring for 30 min. While being maintained at 0° C., the homogeneous solution was slowly added with 69.3 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, unreacted acetonitrile was completely removed from the reaction solution using a rotary evaporator. Then, 600 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was separated by column chromatography using a mixture of ethyl acetate/n-hexane (1:1) as a mobile phase, to obtain 76.5 g of (S)-3-carbamoyl-2-phenyl propanol sulfamates a white solid.

Yield 93%

H-NMR(DMSO, 200 MHz), ppm($\delta$): 3.35(1H,q), 4.16 (2H,d), 4.34(2H,d), 6.57(2H,br), 7.39(5H,s), 7.58(2H,s).

EXAMPLE 75

Preparation of (S)-3-N-Methylcarbamoyl-2-phenyl propanol sulfamate

Except for using (R)-3-N-methylcarbamoyl-2-phenyl propanol, instead of (R)-3-carbamoyl-2-phenyl propanol, as the starting material, the same procedure with that of Example 74 was repeated.

A concentrated reaction mixture thus obtained was separated by column chromatography using a mixture of ethyl acetate/n-hexane (1:1) as a mobile phase, to obtain 77.8 g of (S)-3-N,N'-dimethylcarbamoyl-2-phenyl propanol sulfamate as a white solid.

Yield 90%

H-NMR(DMSO$_3$, 200 MHz), ppm($\delta$): 2.54(3H,d), 3.35 (1H,q), 4.29(4H,m), 6.98(2H,s), 7.29(5H,d), 7.35(2H,s).

EXAMPLE 76

Preparation of (S)-3-N,N'-Dimethylcarbamoyl-2-phenyl propanol sulfamate

Except for using (R)-3-N,N'-dimethylcarbamoyl-2-phenyl propanol, instead of (R)-3-carbamoyl-2-phenyl propanol, as the starting material, the same procedure with that of Example 74 was repeated.

A concentrated reaction mixture thus obtained was separated by column chromatography using a mixture of ethyl acetate/n-hexane (1:1) as a mobile phase, to obtain 79.7 g of (S)-3-N,N'-dimethylcarbamoyl-2-phenyl propanol sulfamate as a white solid.

Yield 88%

H-NMR(CDCl$_3$, 200 MHz), ppm($\delta$): 2.84(6H,d), 3.38 (1H,q), 4.39(4H,m), 4.93(2H,s), 7.21(5H,d).

EXAMPLE 77

Preparation of (S)-3-N-Isopropyl carbamoyl-2-phenyl propanol sulfamate

Except for using (R)-3-N-isopropyl carbamoyl-2-phenyl propanol, instead of (R)-3-carbamoyl-2-phenyl propanol, as the starting material, the same procedure with that of Example 74 was repeated.

A concentrated reaction mixture thus obtained was separated by column chromatography using a mixture of ethyl acetate/n-hexane (1:1) as a mobile phase, to obtain 84.3 g of (S)-3-N-isopropyl carbamoyl-2-phenyl propanol sulfamate as a white solid.

Yield 89%

H-NMR(DMSO, 200 MHz), ppm(δ): 1.01(6H,m), 3.32 (1H,m), 3.55(1H,q), 4.18(2H,d), 4.29(2H,d), 6.95(1H,d), 7.34(5H,s), 7.56(2H,s).

EXAMPLE 78

Preparation of (S)-3-N-Cyclopropyl carbamoyl-2-phenyl propanol sulfamate

Except for using (R)-3-N-cyclopropyl carbamoyl-2-phenyl propanol, instead of (R)-3-carbamoyl-2-phenyl propanol, as the starting material, the same procedure with that of Example 74 was repeated.

A concentrated reaction mixture thus obtained was separated by column chromatography using a mixture of ethyl acetate/n-hexane (1:1) as a mobile phase, to produce 86.7 g of (R)-3-N-cyclopropyl carbamoyl-2-phenyl propanol sulfamate as a white solid.

Yield 92%

H-NMR(DMSO, 200 MHz) ppm(δ): 0.35–0.58(4H,m), 2.51(1H,s), 3.35(1H,q), 4.16–4.36(4H,m), 7.15(1H,br), 7.29 (5H,s), 7.52(2H,s).

EXAMPLE 79

Preparation of (S)-3-N-Morphoryl carbamoyl-2-phenyl propanol sulfamate

Except for using (R)-3-N-morphoryl carbamoyl-2-phenyl propanol, instead of (R)-3-carbamoyl-2-phenyl propanol, as the starting material, the same procedure with that of Example 74 was repeated.

The liquid thus obtained was separated by column chromatography using a mixture of ethyl acetate/n-hexane (1:1) as a mobile phase, to produce 94 g of (S)-3-N-morphorylcarbamoyl-2-phenyl propanol sulfamate as a white solid.

Yield 91%

H-NMR(DMSO, 200 MHz) ppm(δ): 3.05(1H,q), 3.20–3.50(8H,br), 4.15(4H,m), 4.43(2H,s), 7.13(5H,m).

EXAMPLE 80

Preparation of (S)-3-N-Methylcarbamoyl-2-(p-methoxyphenyl)propanol sulfamate

A well dried 2,000 ml flask equipped with a thermometer was purged with nitrogen gas, to completely take off moisture and air from the inside of the flask. This purging was continued for 30 min, after which 1,200 ml of purified acetonitrile was poured into the flask. 71.8 g of (R)-3-N-methylcarbamoyl-2-(p-methoxyphenyl)propanol prepared in Example 73 and 156.8 ml of diisopropyl ethylamine were well dissolved in the solvent and made to be homogeneous by stirring for 30 min. While being maintained at 0° C., the homogeneous solution was slowly added with 69.3 g of sulfamoyl chloride (prepared in the method described in Chem. Ber., 91, 1339–1341 (1958), to Appel and Berger). At the same temperature, the reaction was proceeded and its progress was monitored by thin layer chromatography and liquid chromatography. Roughly, it took about 2 hours to finish the reaction.

After completion of the reaction, acetonitrile remaining was completely removed from the reaction mixture by using a rotary evaporator. (100 ml of distilled water and 600 ml of ethyl acetate were added for solvent extraction. The organic layer thus obtained was dried over anhydrous magnesium sulfate and distilled off the solvent by a rotary evaporator, to give a yellow liquid.

This liquid obtained was separated by column chromatography using a mixture of ethyl acetate/n-hexane (1:1) as a mobile phase, to produce 84 g of (S)-3-N-methylcarbamoyl-2-(p-methoxyphenyl)propanol sulfamate as a white solid.

Yield 88%

H-NMR(DMSO, 200 MHz), ppm (δ): 2.45(3H,d), 3.31 (1H,q), 4.35(4H,m), 6.48(1H,br), 6.89(2H,d), 7.49(2H,s).

The compounds according to the present invention are very useful for the prophylaxis and treatment of CNS disorder, for example, nervous myalgia, epilepsy and minimal brain dysfunction, The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A N,N'-substituted carbamoyl-2-aryl propanol sulfamate racemate, represented by the following formula I:

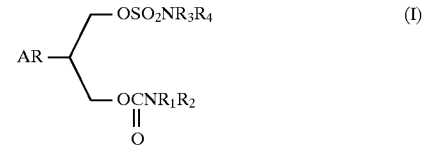

wherein, Ar is represented by the following formulas;

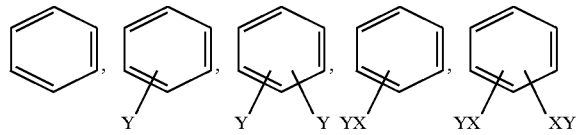

Y is selected from the group consisting of halogens such as F, Cl, Br and I, trifluoromethyl and alkyl groups containing 1 to 3 carbon atoms when Y alone binds to benzene ring and from the group consisting of trifluoromethyl and alkyl groups containing 1 to 3 carbon atoms when Y binds to X which is O or S; and $R_1$, $R_2$, $R_3$ and $R_4$, identical or different, each are selected from the group consisting of hydrogen, linear or branched alkyl groups containing 1 to 16 carbon atoms, cyclic alklyl groups containing 3 to 16 carbon atoms and aryl groups containing 6 to 8 carbon atoms, and $NR_1R_2$ and $NR_3R_4$, identical or different, each may form a 3 to 7-membered aliphatic compound together with another nitrogen atom or oxygen atom.

2. A (R)-N,N'-substituted carbamoyl-2-aryl propanol sulfamate, represented by the following formula II:

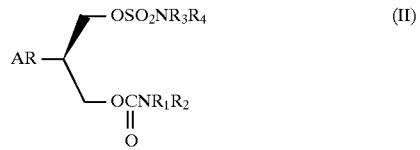 (II)

wherein, Ar is represented by the following formulas;

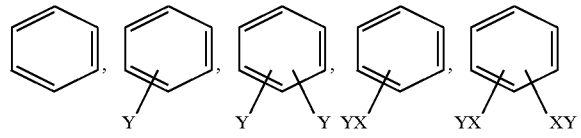

Y is selected from the group consisting of halogens such as F, Cl, Br and I, trifluoromethyl and alkyl groups containing 1 to 3 carbon atoms when Y alone binds to benzene ring and from the group consisting of trifluoromethyl and alkyl groups containing 1 to 3 carbon atoms when Y binds to X which is O or S; and $R_1$, $R_2$, $R_3$ and $R_4$ identical or different, each are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_1R_2$ and $NR_3R_4$, identical or different, each may form a 3 to 7-membered aliphatic compound together with another nitrogen atom or oxygen atom.

3. A (S)-N,N'-substituted carbamoyl-2-aryl propanol sulfamate, represented by the following formula III:

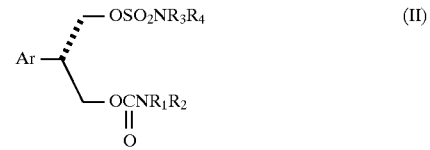 (II)

wherein, Ar is represented by the following formulas;

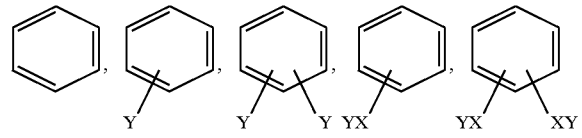

Y is selected from the group consisting of halogens such as F, Cl, Br and I, trifluoromethyl and alkyl groups containing 1 to 3 carbon atoms when Y alone binds to benzene ring and from the group consisting of trifluoromethyl and alkyl groups containing 1 to 3 carbon atoms when Y binds to X which is O or S; and $R_1$, $R_2$, $R_3$ and $R_4$, identical or different, each are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_1R_2$ and $NR_3R_4$, identical or different, each may form a 3 to 7-membered aliphatic compound together with another nitrogen atom or oxygen atom.

* * * * *